(12) United States Patent
Heruth et al.

(10) Patent No.: US 7,542,803 B2
(45) Date of Patent: Jun. 2, 2009

(54) SENSITIVITY ANALYSIS FOR SELECTING THERAPY PARAMETER SETS

(75) Inventors: Kenneth T. Heruth, Edina, MN (US); Keith A. Miesel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 556 days.

(21) Appl. No.: 11/081,873

(22) Filed: Mar. 16, 2005

(65) Prior Publication Data

US 2005/0216064 A1    Sep. 29, 2005

Related U.S. Application Data

(60) Provisional application No. 60/553,769, filed on Mar. 16, 2004.

(51) Int. Cl.
*A61N 1/00* (2006.01)
(52) U.S. Cl. ...................................... 607/46
(58) Field of Classification Search ............... 607/46, 607/4, 5, 9, 2; 600/554, 552, 553, 555, 556
See application file for complete search history.

(56) References Cited

U.S. PATENT DOCUMENTS

| | | | |
|---|---|---|---|
| 4,297,685 A | 10/1981 | Brainard, II | |
| 4,550,736 A | 11/1985 | Broughton et al. | |
| 4,771,780 A | 9/1988 | Sholder | |
| 4,776,345 A | 10/1988 | Cohen et al. | |
| 4,846,195 A | 7/1989 | Alt | |
| 5,040,536 A | 8/1991 | Riff | |
| 5,058,584 A | 10/1991 | Bourgeois | |
| 5,125,412 A | 6/1992 | Thornton | |
| 5,154,180 A | 10/1992 | Blanchet et al. | |
| 5,233,984 A | 8/1993 | Thompson | |
| 5,275,159 A | 1/1994 | Griebel | |
| 5,335,657 A | 8/1994 | Terry, Jr. et al. | |
| 5,337,758 A | 8/1994 | Moore et al. | |

(Continued)

FOREIGN PATENT DOCUMENTS

DE    198 31 109    1/2000

(Continued)

OTHER PUBLICATIONS

M.T. Smith et al., "Presleep Cognitions in Patients with Insomnia Secondary to Chronic Pain," Journal of Behavioral Medicine, vol. 24, No. 1, pp. 93-114, 2001.

(Continued)

*Primary Examiner*—Carl H. Layno
*Assistant Examiner*—Jon-Eric C. Morales
(74) *Attorney, Agent, or Firm*—Shumaker & Sieffert, PA

(57) ABSTRACT

Techniques for controlling delivery of a therapy to a patient by a medical device, such as an implantable medical device (IMD), involve a sensitivity analysis of a performance metric. The performance metric may relate to efficacy or side effects of the therapy. For example, the performance metric may comprise a sleep quality metric, an activity level metric, a movement disorder metric for patients with Parkinson's disease, or the like. The sensitivity analysis identifies values of therapy parameters that defines a substantially maximum or minimum value of the performance metric. The identified therapy parameters are a baseline therapy parameter set, and a medical device may control delivery of the therapy based on the baseline therapy parameter set.

17 Claims, 6 Drawing Sheets

U.S. PATENT DOCUMENTS

| | | | |
|---|---|---|---|
| 5,342,409 A | 8/1994 | Mullett | |
| 5,469,861 A | 11/1995 | Piscopo et al. | |
| 5,476,483 A | 12/1995 | Bornzin et al. | |
| 5,509,927 A * | 4/1996 | Epstein et al. | 607/32 |
| 5,514,162 A | 5/1996 | Bornzin et al. | |
| 5,558,640 A | 9/1996 | Pfeiler et al. | |
| 5,591,216 A * | 1/1997 | Testerman et al. | 607/42 |
| 5,593,431 A | 1/1997 | Sheldon | |
| 5,622,428 A | 4/1997 | Bonnet | |
| 5,645,053 A | 7/1997 | Remmers et al. | |
| 5,683,432 A * | 11/1997 | Goedeke et al. | 607/32 |
| 5,732,696 A | 3/1998 | Rapoport et al. | |
| 5,782,884 A | 7/1998 | Stotts et al. | |
| 5,895,371 A | 4/1999 | Levitas et al. | |
| 5,904,708 A * | 5/1999 | Goedeke | 607/18 |
| 5,919,149 A | 7/1999 | Allum | |
| 5,938,690 A * | 8/1999 | Law et al. | 607/46 |
| 5,941,906 A | 8/1999 | Barreras, Sr. et al. | |
| 5,944,680 A | 8/1999 | Christopherson et al. | |
| 5,999,846 A | 12/1999 | Pardey et al. | |
| 6,044,297 A | 3/2000 | Sheldon et al. | |
| 6,045,513 A | 4/2000 | Stone et al. | |
| 6,059,576 A | 5/2000 | Brann | |
| 6,095,991 A | 8/2000 | Krausman et al. | |
| 6,102,874 A | 8/2000 | Stone et al. | |
| 6,120,467 A | 9/2000 | Schallhorn | |
| 6,128,534 A | 10/2000 | Park et al. | |
| 6,157,857 A | 12/2000 | Dimpfel | |
| 6,161,095 A * | 12/2000 | Brown | 705/2 |
| 6,165,143 A | 12/2000 | van Lummel | |
| 6,259,948 B1 | 7/2001 | Florio et al. | |
| 6,280,409 B1 | 8/2001 | Stone et al. | |
| 6,296,606 B1 | 10/2001 | Goldberg et al. | |
| 6,308,098 B1 | 10/2001 | Meyer | |
| 6,351,672 B1 | 2/2002 | Park et al. | |
| 6,366,813 B1 * | 4/2002 | DiLorenzo | 607/45 |
| 6,416,471 B1 | 7/2002 | Kumar et al. | |
| 6,440,090 B1 | 8/2002 | Schallhorn | |
| 6,449,508 B1 | 9/2002 | Sheldon et al. | |
| 6,459,934 B1 | 10/2002 | Kadhiresan | |
| 6,466,821 B1 | 10/2002 | Pianca et al. | |
| 6,468,234 B1 | 10/2002 | Van der Loos et al. | |
| 6,514,218 B2 | 2/2003 | Yamamoto | |
| 6,539,249 B1 | 3/2003 | Kadhiresan et al. | |
| 6,574,507 B1 | 6/2003 | Bonnet | |
| 6,605,038 B1 | 8/2003 | Teller et al. | |
| 6,611,783 B2 | 8/2003 | Kelly, Jr. et al. | |
| 6,659,968 B1 | 12/2003 | McClure | |
| 6,687,538 B1 | 2/2004 | Hrdlicka et al. | |
| 6,731,984 B2 | 5/2004 | Cho et al. | |
| 6,752,766 B2 | 6/2004 | Kowallik et al. | |
| 6,773,404 B2 | 8/2004 | Poezevera et al. | |
| 6,819,956 B2 | 11/2004 | DiLorenzo | |
| 6,878,121 B2 | 4/2005 | Krausman et al. | |
| 6,881,192 B1 | 4/2005 | Park | |
| 6,884,596 B2 | 4/2005 | Civelli et al. | |
| 6,890,306 B2 | 5/2005 | Poezevera | |
| 6,928,324 B2 | 8/2005 | Park et al. | |
| 6,937,891 B2 * | 8/2005 | Leinders et al. | 607/2 |
| 6,964,641 B2 | 11/2005 | Cho et al. | |
| 7,130,689 B1 | 10/2006 | Turcott | |
| 7,141,034 B2 * | 11/2006 | Eppstein et al. | 604/22 |
| 7,162,304 B1 | 1/2007 | Bradley | |
| 7,209,787 B2 | 4/2007 | DiLorenzo | |
| 2001/0031930 A1 | 10/2001 | Roizen et al. | |
| 2001/0037067 A1 | 11/2001 | Tchou et al. | |
| 2001/0041831 A1 * | 11/2001 | Starkweather et al. | 600/365 |
| 2002/0077562 A1 * | 6/2002 | Kalgren et al. | 600/510 |
| 2002/0091308 A1 | 7/2002 | Kipshidze et al. | |
| 2002/0161412 A1 | 10/2002 | Sun et al. | |
| 2002/0169485 A1 | 11/2002 | Pless et al. | |
| 2002/0177882 A1 | 11/2002 | DiLorenzo | |
| 2002/0193697 A1 | 12/2002 | Cho et al. | |
| 2002/0193839 A1 | 12/2002 | Cho et al. | |
| 2003/0004423 A1 | 1/2003 | Lavie et al. | |
| 2003/0139692 A1 | 7/2003 | Barrey et al. | |
| 2003/0149457 A1 | 8/2003 | Tcheng et al. | |
| 2003/0153953 A1 * | 8/2003 | Park et al. | 607/17 |
| 2003/0153955 A1 | 8/2003 | Park et al. | |
| 2003/0153956 A1 | 8/2003 | Park et al. | |
| 2003/0163059 A1 | 8/2003 | Poezevera et al. | |
| 2003/0171791 A1 * | 9/2003 | KenKnight et al. | 607/60 |
| 2003/0195588 A1 * | 10/2003 | Fischell et al. | 607/55 |
| 2003/0212445 A1 | 11/2003 | Weinberg | |
| 2004/0002741 A1 | 1/2004 | Weinberg | |
| 2004/0002742 A1 | 1/2004 | Florio | |
| 2004/0015103 A1 | 1/2004 | Aminian et al. | |
| 2004/0049132 A1 | 3/2004 | Barron et al. | |
| 2004/0077995 A1 * | 4/2004 | Ferek-Petric et al. | 604/66 |
| 2004/0102814 A1 | 5/2004 | Sorensen et al. | |
| 2004/0111040 A1 | 6/2004 | Ni et al. | |
| 2004/0111041 A1 | 6/2004 | Ni et al. | |
| 2004/0220621 A1 * | 11/2004 | Zhou et al. | 607/2 |
| 2005/0021103 A1 | 1/2005 | DiLorenzo | |
| 2005/0021104 A1 | 1/2005 | DiLorenzo | |
| 2005/0042589 A1 | 2/2005 | Hatlestad et al. | |
| 2005/0113710 A1 | 5/2005 | Stahmann et al. | |
| 2005/0119703 A1 | 6/2005 | DiLorenzo | |
| 2005/0177192 A1 | 8/2005 | Rezai et al. | |
| 2005/0209511 A1 | 9/2005 | Heruth et al. | |
| 2005/0209512 A1 | 9/2005 | Heruth et al. | |
| 2005/0209513 A1 | 9/2005 | Heruth et al. | |
| 2005/0209643 A1 | 9/2005 | Heruth et al. | |
| 2005/0209644 A1 | 9/2005 | Heruth et al. | |
| 2005/0209645 A1 | 9/2005 | Heruth et al. | |
| 2005/0215847 A1 | 9/2005 | Heruth et al. | |
| 2005/0215947 A1 | 9/2005 | Heruth et al. | |
| 2005/0216064 A1 | 9/2005 | Heruth et al. | |
| 2005/0222522 A1 | 10/2005 | Heruth et al. | |
| 2005/0222626 A1 | 10/2005 | DiLorenzo | |
| 2005/0222643 A1 | 10/2005 | Heruth et al. | |
| 2005/0234514 A1 | 10/2005 | Heruth et al. | |
| 2005/0234518 A1 | 10/2005 | Heruth et al. | |
| 2005/0240086 A1 | 10/2005 | Akay | |
| 2005/0240242 A1 | 10/2005 | DiLorenzo | |
| 2005/0245790 A1 | 11/2005 | Bergfalk et al. | |
| 2005/0245988 A1 | 11/2005 | Miesel | |
| 2006/0224191 A1 | 10/2006 | DiLorenzo | |
| 2006/0293720 A1 | 12/2006 | DiLorenzo | |
| 2007/0073355 A1 | 3/2007 | DiLorenzo | |
| 2007/0142862 A1 | 6/2007 | DiLorenzo | |

FOREIGN PATENT DOCUMENTS

| | | |
|---|---|---|
| DE | 100 24 103 | 11/2001 |
| EP | 0 564 803 | 10/1993 |
| EP | 0 849 715 B1 | 6/1998 |
| EP | 1 195 139 | 4/2002 |
| EP | 1 195 139 A1 | 4/2002 |
| EP | 1 291 036 | 3/2003 |
| EP | 1 308 182 | 5/2003 |
| EP | 1 308 182 A2 | 5/2003 |
| EP | 1 437 159 | 7/2004 |
| EP | 1 437 159 A1 | 7/2004 |
| EP | 1 322 227 B1 | 12/2005 |
| GB | 2 330 912 | 5/1999 |
| WO | WO 98/00197 | 1/1998 |
| WO | WO 99/13765 | 3/1999 |
| WO | WO 01/37930 | 5/2001 |
| WO | WO 02/28282 | 4/2002 |
| WO | WO 02/041771 | 5/2002 |
| WO | WO 02/087433 | 11/2002 |
| WO | WO 02/096512 | 12/2002 |
| WO | WO 02/100267 | 12/2002 |

| | | |
|---|---|---|
| WO | WO 03/024325 | 3/2003 |
| WO | WO 03/051356 | 6/2003 |
| WO | WO 03/065891 | 8/2003 |
| WO | WO 2005/028029 | 3/2005 |
| WO | WO 2005/035050 | 4/2005 |

OTHER PUBLICATIONS

M.T. Smith et al., "How do sleep disturbance and chronic pain interrelate? Insights from the longitudinal and cognitive-behavioral clinical trials literature," Sleep Medicine Reviews, YSMRV 286, pp. 1-14, Jun. 19, 2003.

Suanne Goodrich et al., "The Prediction of Pain Using Measures of Sleep Quality," Pain Digest (1998) 8:23-25.

"Analysis of heart rate dynamics by methods derived from nonlinear mathematics: Clinical applicability and prognostic significance" http:/herkules.oulu.fi.isbn9514250133/html/x222.html, 4 pgs. (downloaded 2004).

International Search Report and Written Opinion for corresponding PCT Application Serial No. PCT/US2005/008698, mailed Jul. 26, 2005 (9 pgs.).

"Watch," Wikipedia, the free encyclopedia, 6 pgs., http://en.wikipedia.org/wiki/Watch, (2006).

"IBM & Citizen Watch develop Linux-based 'WatchPad'," 5 pgs., http://www.linuxdevices.com/news/NS6580187845.html, (2006).

Tuisku, Katinka, "Motor Activity Measured By Actometry in Neuropsychiatric Disorders," Department of Psychiatry, University of Helsinki, Helsinki, Finland, 115 pgs., (2002).

Kassam, M., "2005 EDP Topic 'MK4': Tremor Data-Logger for Parkinson's Disease Patients," http://www.ee.ryerson.ca/~courses/edp2005/MK4.html, 3 pgs., (2006).

"Design Competition: Runners-Up for the Best Three Designs," EPN, vol. 26, No. 1, (2002).

"MiniMitter® Physiological and Behavioral Monitoring for Humans and Animals," http://www.minimitter.com/Products/Actiwatch, 3 pgs., (2006).

Notification of Transmittal of the International Preliminary Report on Patentability for corresponding PCT Application Serial No. PCT/US2005/008698, dated Mar. 16, 2006, 10 pgs.

Amzica, "Physiology of Sleep and Wakefulness as it Relates to the Physiology of Epilepsy," Journal of Clinical Neurophysiology, American Clinical Neurophysiology Society, 19(6), pp. 488-503, (2002).

Dinner, "Effect of Sleep on Epilepsy," Journal of Clinical Neurophysiology, American Clinical Neurophysiology Society, 19(6), pp. 504-513, (2002).

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, (2002).

Mendez et al. "Interactions Between Sleep and Epilepsy," Journal of Clinical Neurphysiology, American Clinical Neurophysiology Society, 18(2), pp. 106-127, (2001).

Kerr et al., "Analysis of the sit-stand-sit movement cycle in normal subjects," Clinical Biomechanics, vol. 12, No. 4, pp. 236-245, (1997).

Aminian et al. "Physical Activity Monitoring Based on Accelerometry: Validation and Comparison with Video Observation," Medical & Biological Engineering & Computing, vol. 37, No. 2, pp. 304-308 (1999).

Medcare—A Global Leader in Sleep Diagnostics, Embletta Recording System, http://www.medcare.com/products/diagnostic/embletta/, 2 pgs. Jan. 31, 2005.

Medcare—A Global Leader in Sleep Diagnostics, Somnologica for Embletta, http://www.medcare.com/products/diagnostic/embletta/SomnoEmbletta/index.asp, 1 pg. Jan. 31, 2005.

MAP Medizin-Technologie GmbH, Poly-MESAM®, http://195.244.124.130/map/de/eng/map_med.nsf/cmsall/70564A3FCBE4188AC1256EF4 . . . , 4 pgs. Jan. 31, 2005.

Merlin, http://www.aha.ru/~pir/english/merlin/, 4 pgs. Jan. 31, 2005.

Sleep Solutions—PR Newswire: Sleep Solutions Introduces NovaSom™ QSG™ for PSG . . . , http://www.sleep-solutions.com/press_room/novasom.htm, 2 pgs. Jan. 31, 2005.

Itamar Medical Information, http://itamar-medical.com/content.asp?id-id=31, 2 pgs. Jan. 31, 2005.

Criticare System Inc.,-504DX Portable Pulse Oximeter, http://www.csiusa.com/504dx.html, 4 pgs. Jan. 31, 2005.

Snap® Laboratories, Product Fact Sheet, http://www.snaplab.com/mp_fact.htm, 2 pgs. Jan. 31, 2005.

Sleep Strip & Bite Strip, http://www.quietsleep.com/snoringapnea/sleepstrip.htm, 8 pgs. Jan. 31, 2005.

"Bitestrip Flier," downloaded from Internet Archive of www.quietsleep.com dated Jan. 29, 2005 http://web.archive.org/web/20041124080003/www.quietsleep.com/pdf/Bitestrip+Flier.pdf.

"Bilateral Comparisons of the BiteStrip Bruxism Device and Masseter EMG Bruxism Events" downloaded from Internet Archive of www.quietsleep.com dated Jan. 29, 2005 http://web.archive.org/web/20041124075114/www.quietsleep.com/pdf/Bilateral+Comparisons.pdf.

"The BiteStrip: A Novel Screener for Sleep Bruxism," downloaded from Internet Archive of www.quietsleep.com dated Jan. 29, 2005 http://web.archive.org/web/20041124072922/www.quietsleep.com/pdf/BiteStrip-+Novel+Screener.pdf.

Office Action dated Jul. 20, 2006 for U.S. Appl. No. 10/825,955, filed Apr. 15, 2004, (10 pgs.).

Responsive Amendment dated Oct. 20, 2006 for U.S. Appl. No. 10/825,955, filed Apr. 15, 2004 (21 pgs.).

Office Action dated Jan. 17, 2007 for U.S. Appl. No. 10/825,955, filed Apr. 15, 2004, (10 pgs.).

Responsive Amendment dated Mar. 19, 2007 for U.S. Appl. No. 10/825,955, filed Apr. 15, 2004 (13 pgs.).

Office Action dated Jun. 27, 2007 for U.S. Appl. No. 10/825,955, filed Apr. 15, 2004, (13 pgs.).

Office Action dated Jul. 5, 2006 for U.S. Appl. No. 10/825,953, filed Apr. 15, 2004, (11 pgs.).

Responsive Amendment dated Oct. 5, 2006 for U.S. Appl. No. 10/825,953, filed Apr. 15, 2004 (17 pgs.).

Office Action dated Dec. 28, 2006 for U.S. Appl. No. 10/825,953, filed Apr. 15, 2004, (9 pgs.).

Response dated Feb. 28, 2007 for U.S. Appl. No. 10/825,953, filed Apr. 15, 2004 (7 pgs.).

Office Action dated Apr. 3, 2007 for U.S. Appl. No. 10/825,953, filed Apr. 15, 2004, (8 pgs.).

Responsive Amendment dated Jun. 28, 2007 for U.S. Appl. No. 10/825,953, filed Apr. 15, 2004 (19 pgs.).

Office Action dated Jul. 3, 2007 for U.S. Appl. No. 10/826,925, filed Apr. 15, 2004, (22 pgs.).

Office Action dated May 5, 2008 for U.S. Appl. No. 10/826,925 (12 pgs.).

Office Action dated May 30, 2008 for U.S. Appl. No. 11/081,811 (13 pgs.).

Office Action dated May 6, 2008 for U.S. Appl. No. 10/825,955 (13 pgs.).

Response to Office Action dated Jul. 2, 2008 for U.S. Appl. No. 10/825,955 (13 pgs.).

Office Action dated May 9, 2008 for U.S. Appl. No. 11/081,857 (10 pgs.).

Office Action dated Apr. 4, 2008 for U.S. Appl. No. 11/081,155 (9 pgs.).

Responsive Amendment dated Aug. 4, 2008 for U.S. Pat. Appl. No. 11/081,155 (12 pgs.).

Responsive Amendment dated Aug. 7, 2008 for U.S. Pat. Appl. No. 11/081,857 (13 pgs.).

Response dated Aug. 4, 2008 for U.S. Pat. Appl. No. 11/826,925 (7 pgs.).

Responsive Amendment dated Aug. 29, 2008 for U.S. Pat. Appl. No. 11/081,811 (13 pgs.).

* cited by examiner

SENSITIVITY ANALYSIS FOR SELECTING THERAPY PARAMETER SETS

This application claims the benefit of U.S. Provisional Application Ser. No. 60/553,769, filed Mar. 16, 2004, the entire content of which is incorporated herein by reference.

TECHNICAL FIELD

The invention relates to medical devices and, more particularly, to medical devices that deliver a therapy.

BACKGROUND

In some cases, an ailment may affect a patient's sleep quality or physical activity level, or a therapy delivered to the patient to treat the ailment may produce undesirable side effects. For example, chronic pain may cause a patient to have difficulty falling asleep, and may disturb the patient's sleep, e.g., causing the patient to wake. Further, chronic pain may cause the patient to have difficulty achieving deeper sleep states, such as one of the nonrapid eye movement (NREM) sleep states associated with deeper sleep. Other ailments that may negatively affect patient sleep quality include movement disorders, psychological disorders, sleep apnea, congestive heart failure, gastrointestinal disorders and incontinence. As another example, chronic pain may cause a patient to avoid particular physical activities, or activity in general, where such activities increase the pain experienced by the patient. Movement disorders and congestive heart failure may also affect patient activity level.

Furthermore, in some cases, poor sleep quality may increase the symptoms experienced by a patient due to an ailment. For example, poor sleep quality has been linked to increased pain symptoms in chronic pain patients. The link between poor sleep quality and increased symptoms is not limited to ailments that negatively impact sleep quality, such as those listed above. Nonetheless, the condition of a patient with such an ailment may progressively worsen when symptoms disturb sleep quality, which in turn increases the frequency and/or intensity of symptoms.

In some cases, these ailments are treated via a medical device, such as an implantable medical device (IMD). For example, patients may receive an implantable neurostimulator or drug delivery device to treat chronic pain or a movement disorder. Congestive heart failure may be treated by, for example, a cardiac pacemaker.

SUMMARY

In general, the invention is directed to systems, devices and techniques for controlling delivery of a therapy to a patient by a medical device, such as an implantable medical device (IMD), based on a sensitivity analysis of a performance metric. The performance metric may relate to efficacy or side effects associated with a particular therapy. For example, the performance metric may comprise a sleep quality metric, an activity level metric, a posture metric, a movement disorder metric for patients with Parkinson's disease, a side-effects metric, or the like. The sensitivity analysis facilitates generation of a therapy parameter set that defines a substantially maximum or minimum value of the performance metric. A medical device according to an embodiment of the invention may conduct the sensitivity analysis for the performance metric, and identify values for each of a plurality of physiological parameters based on the sensitivity analysis. A system according to an embodiment of the invention may include a monitor, a programmer, and a therapy device to conduct the sensitivity analysis for the performance metric, and determine a baseline therapy parameter set based on the sensitivity analysis. In either case, the medical device or another medical device may control delivery of the therapy based on a baseline therapy parameter set that includes the identified values. The baseline therapy parameter set may be a therapy parameter set found to be most efficacious or to result in the least side effects, as indicated by the performance metric value associated with that therapy parameter set.

For the sensitivity analysis, a medical device may deliver therapy according to a plurality of different therapy parameter sets. Each of the therapy parameter sets comprises a value for each of a plurality of therapy parameters. The plurality of therapy parameter sets for the sensitivity analysis encompass a range of therapy parameter values. The therapy parameter sets may be generated either randomly or non-randomly. The therapy parameter sets may be defined, for example, by the medical device or an external programming device. The medical device, programming device, or another device may monitor performance metric values for each therapy parameter set in order to conduct the sensitivity analysis.

Furthermore, after a baseline therapy parameter set has been identified, the medical device that delivers therapy according to the baseline therapy parameter set may periodically perturb at least one therapy parameter value of the baseline therapy parameter set to determine whether the performance metric value has changed over time. The therapy parameter may be increased or decreased in small increments relative to the range values. If perturbing the therapy parameter improves the performance metric, the therapy parameter value is further increased or decreased to again define a substantially maximum or minimum performance metric value. The baseline therapy parameter set is then updated to correspond to the therapy parameter set with the perturbed therapy parameter value or values. If changing the therapy parameter worsens the performance metric, the baseline therapy parameter set is maintained. The medical device that delivers therapy according to the baseline therapy parameter set, a programming device, or another device may determine the performance metric values for each perturbation, and update the baseline therapy parameter set if indicated by the comparison to the performance metric value for the baseline therapy parameter set.

The medical device or a separate monitor, as examples, may monitor one or more physiological parameters of the patient in order to determine values for the one or more performance metrics. Example physiological parameters that the medical device may monitor include activity level, posture, heart rate, ECG morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, eye motion, and galvanic skin response. These parameters may be indicative of sleep quality and activity level, and therefore may be useful in determining the performance metric values for different therapy parameter sets. In some embodiments, the medical device additionally or alternatively monitors the variability of one or more of these parameters. In order to monitor one or more of these parameters, the medical device may include, be coupled to, or be in wireless communication with one or more sensors, each of which outputs a signal as a function of one or more of these physiological parameters.

In one embodiment, the invention is directed to a method comprising delivering a therapy to a patient via a medical device according to each of a plurality of therapy parameter sets, each of the therapy parameter sets including a value for each of a plurality of therapy parameters, and monitoring a value of a performance metric of a patient in response to therapy delivered according to each of a plurality of therapy parameter sets. The method further comprises conducting a sensitivity analysis of the performance metric for each of the plurality of therapy parameter sets, and identifying a baseline value for each of the therapy parameters based on the sensitivity analysis to form a baseline therapy parameter set.

In another embodiment, the invention is directed to a medical device that includes a therapy module and a processor. The therapy module delivers a therapy to a patient according to each of a plurality of therapy parameter sets, each of the therapy parameter sets including a value for each of a plurality of therapy parameters. The processor monitors a value of a performance metric of the patient in response to therapy delivered according to each of a plurality of therapy parameter sets. The processor further conducts a sensitivity analysis of the performance metric for each of the plurality of therapy parameter sets, and identifies a baseline value for each of the therapy parameters based on the sensitivity analysis to form a baseline therapy parameter set.

In another embodiment, the invention is directed to a computer-readable medium containing instructions. The instructions cause a programmable processor to monitor a value of a performance metric of a patient for each of a plurality of therapy parameter sets, wherein a medical device delivers a therapy to the patient according to each of the therapy parameters sets, and each of the parameter sets includes a value for each of a plurality of therapy parameters. The instructions further cause the processor to conduct a sensitivity analysis of the performance metric for each of the plurality of therapy parameter sets, and identify a baseline value for each of the plurality of therapy parameters based on the sensitivity analysis to form a baseline therapy parameter set.

In another embodiment, the invention is directed to a system comprising a therapy device, a monitor, and a computing device. The therapy device delivers therapy to a patient according to each of a plurality of therapy parameter sets, each of the therapy parameter sets including a value for each of a plurality of therapy parameters. The monitor monitors values of at least one physiological parameter of a patient in response to therapy delivered according to each of the plurality of therapy parameter sets. The computing device receives the physiological parameter values from the monitor, identifies values of a performance metric of the patient for each of the plurality of parameter sets based on the physiological parameter values monitored during delivery of therapy according to each of the plurality of therapy parameter sets, conducts a sensitivity analysis of the performance metric for each of the plurality of therapy parameter sets, and identifies a baseline value for each of the therapy parameters based on the sensitivity analysis to form a baseline therapy parameter set.

The invention is capable of providing one or more advantages. For example, through the sensitivity analysis of the performance metric, a baseline therapy parameter set that provides substantially maximum or minimum value of the performance metric may be identified. A medical device may provide therapy according to the baseline therapy parameter set.

Further, the medical device may be able to adjust therapy to produce an improved performance metric value. In particular, the adjustments may address symptoms that cause a poor performance metric value or symptoms that are worsened by a poor performance metric value. Adjusting therapy based on the performance metric value information may significantly improve the patient's performance quality and condition. The ability of a medical device to periodically check performance metric values and adjust therapy parameters based on the performance metric values may reduce the need for the patient to make time consuming and expensive clinic visits when the patient's sleep is disturbed, physical activity level has decreased, or symptoms have worsened.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
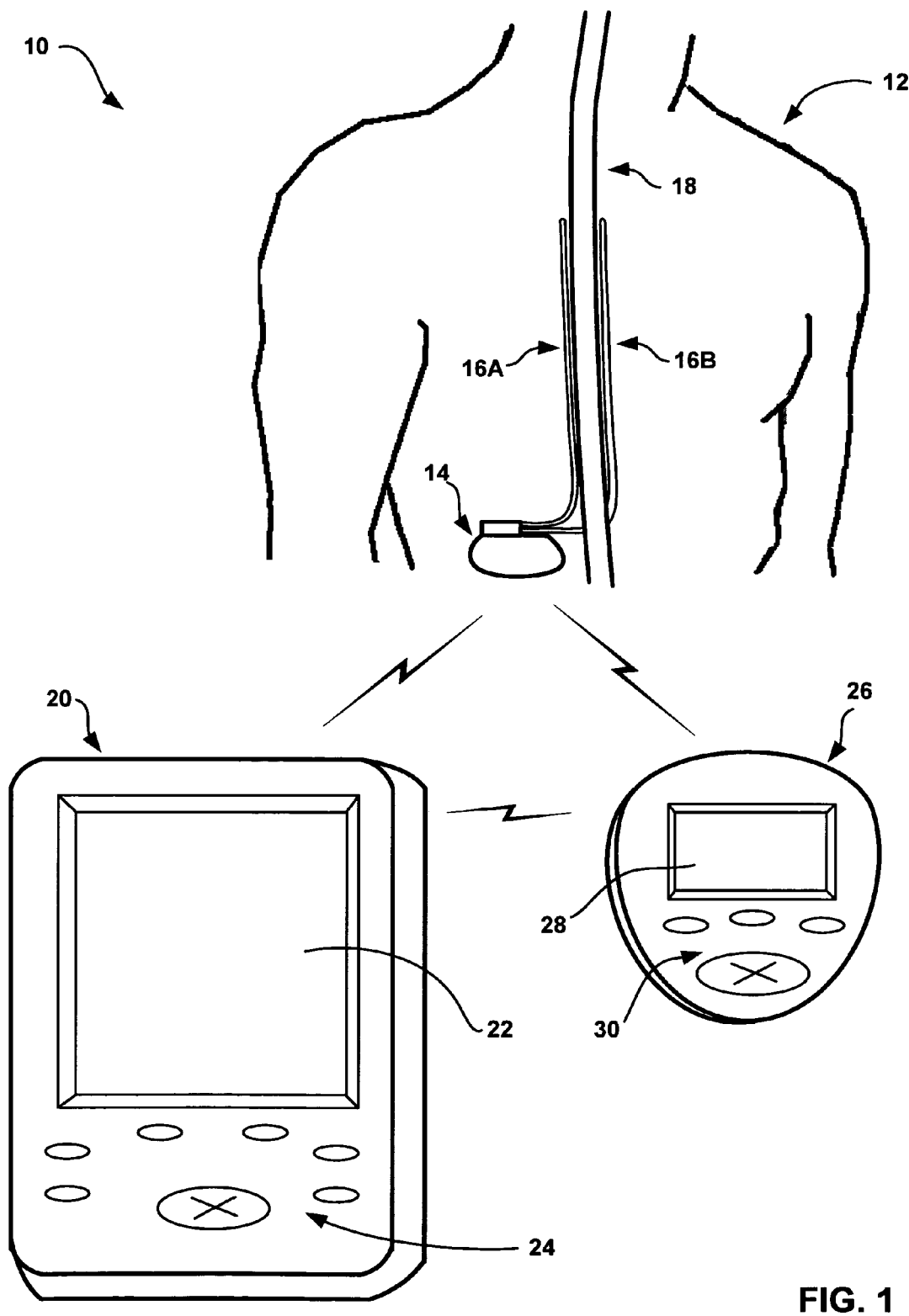
FIG. 1 is a conceptual diagram illustrating an example system that includes an implantable medical device that controls delivery of therapy based on a sensitivity analysis of a performance metric.

FIG. 1 is a conceptual diagram illustrating an example system 10 that includes an implantable medical device (IMD) 14 that controls delivery of a therapy to a patient 12 based on a sensitivity analysis of a performance metric. The performance metric may relate to efficacy or side effects. For example, the performance metric may comprise a sleep quality metric, a physical activity level metric, a posture metric, a movement disorder metric for patients with Parkinson's disease, or the like. The sensitivity analysis determines values of a therapy parameter set that define a substantially maximum or minimum value of the performance metric. In particular, as will be described in greater detail below, IMD 14 or another device conducts the sensitivity analysis of the performance metric, and determines a baseline therapy parameter set based on the sensitivity analysis. IMD 14 controls delivery of the therapy based on the baseline therapy parameter set. Furthermore, IMD 14 or another device may periodically perturb at least one therapy parameter value of the baseline therapy parameter set to determine whether the performance metric value has changed over time.

Feedback entered by patient 12, such as comments and/or a pain level value, may also be used as a performance metric to determine the baseline therapy parameter set. In some cases, a clinician or physician may determine a weighting scheme to provide more or less significance to the patient's feedback, i.e., the physician may choose to give the patient feedback zero weight and instead rely completely on other performance metric values, or the physician may judge that the patient has enough perspective to be able to competently gage pain levels and input substantially objective feedback into the sensitivity analysis.

Although the invention may use any performance metric, for purposes of illustration, the invention will be described herein as using a sleep quality metric to control the delivery of therapy to a patient. IMD 14 may be able to adjust the therapy to address symptoms causing disturbed sleep, or symptoms that are worsened by disturbed sleep. In exemplary embodiments, IMD 14 delivers a therapy to treat chronic pain, which may both negatively impact the quality of sleep experienced by patient 12, and be worsened by inadequate sleep quality.

In the illustrated example system, IMD 14 takes the form of an implantable neurostimulator that delivers neurostimulation therapy in the form of electrical pulses to patient 12. IMD 14 delivers neurostimulation therapy to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12.

However, the invention is not limited to the configuration of leads 16 shown in FIG. 1, or to the delivery of SCS therapy. For example, one or more leads 16 may extend from IMD 14 to the brain (not shown) of patient 12, and IMD 14 may deliver deep brain stimulation (DBS) therapy to patient 12 to, for example, treat tremor or epilepsy. As further examples, one or more leads 16 may be implanted proximate to the pelvic nerves (not shown) or stomach (not shown), and IMD 14 may deliver neurostimulation therapy to treat incontinence, sexual dysfunction, or gastroparesis.

Moreover, the invention is not limited to implementation via an implantable neurostimulator, or even implementation via an IMD. In other words, any implantable or external medical device that delivers a therapy may control delivery of the therapy based on performance metric information, such as sleep quality information, according to the invention.

Further, the invention is not limited to embodiments in which the therapy-delivering medical device performs the sensitivity analysis. For example, in some embodiments, a computing device, such as a programming device, controls testing of therapy parameter sets by a therapy-delivering medical device, receives performance metric values from the medical device, performs the sensitivity analysis, and provides a baseline therapy parameter set to the therapy-delivering medical device. In some embodiments, multiple computing devices may cooperate to perform these functions. For example, a programming device may control testing of therapy parameter sets by the therapy-delivering medical device and receive performance metric values from the medical device, while another computing device performs the sensitivity analysis on the performance metric values, and identifies the baseline therapy parameter set. The other computing device may provide the baseline therapy parameter set to the programming device, which may in turn provide the baseline therapy parameter set to the medical device. The other computing device may have a greater computing capacity than the programming device, which may allow it to more easily perform the sensitivity analysis, and may, for example, be a server coupled to the programming device by a network, such as a local area network (LAN), wide area network (WAN), or the Internet.

As another example, in some embodiments, the programming device or other computing device may receive values for one or more physiological parameters from the medical device, and may determine values for the performance metric based on the physiological parameter values. Further, in some embodiments of the invention, an implantable or external monitor separate from the therapy-delivering medical device may monitor physiological parameters of the patient instead of, or in addition to the therapy-delivering medical device. The monitor may determine values of the performance metric based on values of the physiological parameters, or transmit the physiological parameter values to a programming device or other computing device that determines the values of the performance metric. In some embodiments, the programming device and the monitor may be embodied within a single device.

Additionally, in some embodiments, a therapy device other than IMD 14 may deliver therapy during the process of determining the baseline therapy parameter sets. The other therapy device may be an external or implantable trialing device, such as a trial neurostimulator or trial pump. The other therapy delivery device may monitor physiological parameter values of patient 12, determine performance metric values, and perform the sensitivity analysis, as described herein with reference to IMD 14. In other embodiments, some or all of these functions may be performed by a monitor, programming device, or other computing device, as described above. In such embodiments, IMD 14 may deliver therapy according to a baseline therapy parameter set determined by a sensitivity analysis during a trialing period, and may perturb the therapy parameters for continued refinement of the baseline therapy parameter set, as will be described in greater detail below.

In the illustrated embodiment, IMD 14 delivers therapy according to a set of therapy parameters, i.e., a set of values for a number of parameters that define the therapy delivered according to that therapy parameter set. In embodiments where IMD 14 delivers neurostimulation therapy in the form of electrical pulses, the parameters may include voltage or current pulse amplitudes, pulse widths, pulse rates, duty cycles, durations, and the like. Further, each of leads 16 includes electrodes (not shown in FIG. 1), and a therapy parameter set may include information identifying which electrodes have been selected for delivery of pulses, and the polarities of the selected electrodes. Therapy parameter sets used by IMD 14 may include a number of parameter sets programmed by a clinician (not shown), and parameter sets representing adjustments made by patient 12 to these preprogrammed sets.

In other non-neurostimulator embodiments of the invention, the IMD 14 may still deliver therapy according to a different type of therapy parameter set. For example, implantable pump IMD embodiments may deliver a therapeutic agent to a patient according to a therapy parameter set that includes, for example, a dosage, an infusion rate, and/or a duty cycle.

System 10 also includes a clinician programmer 20, which is an example of a programming device that may determine values of a performance metric and/or perform a sensitivity analysis, as described above. A clinician (not shown) may use clinician programmer 20 to program therapy for patient 12, e.g., specify a number of therapy parameter sets and provide the parameter sets to IMD 14. The clinician may also use clinician programmer 20 to retrieve information collected by IMD 14. The clinician may use clinician programmer 20 to communicate with IMD 14 both during initial programming of IMD 14, and for collection of information and further programming during follow-up visits.

Clinician programmer 20 may, as shown in FIG. 1, be a handheld computing device. Clinician programmer 20 includes a display 22, such as a LCD or LED display, to display information to a user. Clinician programmer 20 may also include keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus, mouse, or the like. Keypad 24 may take the form of a complete keyboard, an alphanumeric keypad or a reduced set of keys associated with particular functions.

System 10 also includes a patient programmer 26, which also may, as shown in FIG. 1, be a handheld computing device. Patient 12 may use patient programmer 26 to control the delivery of therapy by IMD 14. For example, using patient programmer 26, patient 12 may select a current therapy parameter set from among the therapy parameter sets preprogrammed by the clinician, or may adjust one or more parameters of a preprogrammed therapy parameter set to arrive at the current therapy parameter set. As an example, patient 12 may increase or decrease stimulation pulse amplitude using patient programmer 26. Patient programmer 26 is also an example of a programming device that may determine values of a performance metric and/or perform a sensitivity analysis, as described above.

Patient programmer 26 may also include a display 28 and a keypad 30 to allow patient 12 to interact with patient programmer 26. In some embodiments, display 28 may be a touch screen display, and patient 12 may interact with patient programmer 26 via display 28. Patient 12 may also interact with patient programmer 26 using peripheral pointing devices, such as a stylus, mouse, or the like.

However, clinician and patient programmers 20, 26 are not limited to the hand-held computer embodiments illustrated in FIG. 1. Programmers 20, 26 according to the invention may be any sort of computing device. For example, a programmer 20, 26 according to the invention may a tablet-based computing device, a desktop computing device, or a workstation.

IMD 14, clinician programmer 20 and patient programmer 26 may, as shown in FIG. 1, communicate via wireless communication. Clinician programmer 20 and patient programmer 26 may, for example, communicate via wireless communication with IMD 14 using radio frequency (RF) or infrared telemetry techniques known in the art. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols.

Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, communicating via a local area network (LAN), wide area network (WAN), public switched telephone network (PSTN), or cellular telephone network, for example.

As mentioned above, IMD 14 controls delivery of a therapy, e.g., neurostimulation, to patient 12 based on a sensitivity analysis of the sleep quality experienced by the patient. In some embodiments, as will be described in greater detail below, IMD 14 conducts the sensitivity analysis to determine values of a therapy parameter set that defines a substantially maximum value of a sleep quality metric that indicates the quality of sleep experienced by patient 12. IMD 14 determines a baseline therapy parameter set based on the sensitivity analysis and controls delivery of the therapy to patient 12, e.g., adjusts the therapy, based on the baseline therapy parameter set. Furthermore, IMD 14 may periodically perturb at least one therapy parameter value of the baseline therapy parameter set to determine whether the response of the sleep quality metric value to perturbation has changed over time. The perturbation may occur at a preset time, in response to a change in a physiological parameter of a patient, or in response to a signal from a patient or a clinician. The therapy parameter values may be increased or decreased in small increments relative the therapy parameter range.

In some embodiments, IMD 14 compares the sleep quality metric value defined by the baseline therapy parameter set to a sleep quality metric value defined by the perturbed therapy parameter values. IMD 14 then adjusts the therapy delivered to patient 12 based on the comparison. For example, IMD 14 may maintain the baseline therapy parameter set when the comparison shows no improvement in the value of the sleep quality metric during perturbation. When the comparison shows improvement in the sleep quality metric value during perturbation, IMD 14 updates the baseline therapy parameter set based on the one or more perturbed therapy parameter values.

In other embodiments, an implantable or external programmer, such as programmers 20 and 26, may perturb at least one therapy parameter value of the baseline therapy parameter set and an implantable or external monitoring device may monitor the sleep quality metric value. The programmer may also conduct the comparison and update the baseline parameter set based on the comparison. An implantable or external therapy device, such as IMD 14, may then alter the therapy provided to the patient based on the updated baseline parameter set.

IMD 14 may monitor one or more physiological parameters of the patient in order to determine values for one or more sleep quality metrics. Example physiological parameters that IMD 14 may monitor include activity level, posture, heart rate, ECG morphology, respiration rate, respiratory volume, blood pressure, blood oxygen saturation, partial pressure of oxygen within blood, partial pressure of oxygen within cerebro spinal fluid, muscular activity and tone, core temperature, subcutaneous temperature, arterial blood flow, brain electrical activity, and eye motion. Some external medical device embodiments of the invention may additionally or alternatively monitor galvanic skin response. Further, in some embodiments, IMD 14 additionally or alternatively monitors the variability of one or more of these parameters. In order to monitor one or more of these parameters, IMD 14 may include, be coupled to, or be in wireless communication with one or more sensors (not shown in FIG. 1), each of which outputs a signal as a function of one or more of these physiological parameters.

For example, IMD 14 may determine sleep efficiency and/or sleep latency values. Sleep efficiency and sleep latency are example sleep quality metrics. IMD 14 may measure sleep efficiency as the percentage of time while patient 12 is attempting to sleep that patient 12 is actually asleep. IMD 14 may measure sleep latency as the amount of time between a first time when patient 12 begins attempting to sleep and a second time when patient 12 falls asleep, e.g., as an indication of how long it takes patient 12 to fall asleep.

IMD 14 may identify the time at which patient begins attempting to fall asleep in a variety of ways. For example, IMD 14 may receive an indication from the patient that the patient is trying to fall asleep via patient programmer 26. In other embodiments, IMD 14 may monitor the activity level of patient 12, and identify the time when patient 12 is attempting to fall asleep by determining whether patient 12 has remained inactive for a threshold period of time, and identifying the time at which patient 12 became inactive. In still other embodiments, IMD 14 may monitor the posture of patient 12, and may identify the time when the patient 12 becomes recumbent, e.g., lies down, as the time when patient 12 is attempting to fall asleep. In these embodiments, IMD 14 may also monitor the activity level of patient 12, and confirm that patient 12 is attempting to sleep based on the activity level.

IMD 14 may identify the time at which patient 12 has fallen asleep based on the activity level of the patient and/or one or more of the other physiological parameters that may be monitored by IMD 14 as indicated above. For example, IMD 14 may identify a discernable change, e.g., a decrease, in one or more physiological parameters, or the variability of one or more physiological parameters, which may indicate that patient 12 has fallen asleep. In some embodiments, IMD 14 determines a sleep probability metric value based on a value of a physiological parameter monitored by the medical device. In such embodiments, the sleep probability metric value may be compared to a threshold to identify when the patient has fallen asleep. In some embodiments, a sleep probability metric value is determined based on a value of each of a plurality of physiological parameters, the sleep probability values are averaged or otherwise combined to provide an overall sleep probability metric value, and the overall sleep probability metric value is compared to a threshold to identify the time that the patient falls asleep.

Other sleep quality metrics include total time sleeping per day, and the amount or percentage of time sleeping during nighttime or daytime hours per day. In some embodiments, IMD 14 may be able to detect arousal events and apneas occurring during sleep based on one or more monitored physiological parameters, and the number of apnea and/or arousal events per night may be determined as a sleep quality metric. Further, in some embodiments, IMD 14 may be able to determine which sleep state patient 12 is in based on one or more monitored physiological parameters, e.g., rapid eye movement (REM), S1, S2, S3, or S4, and the amount of time per day spent in these various sleep states may be a sleep quality metric.

Figure 2:
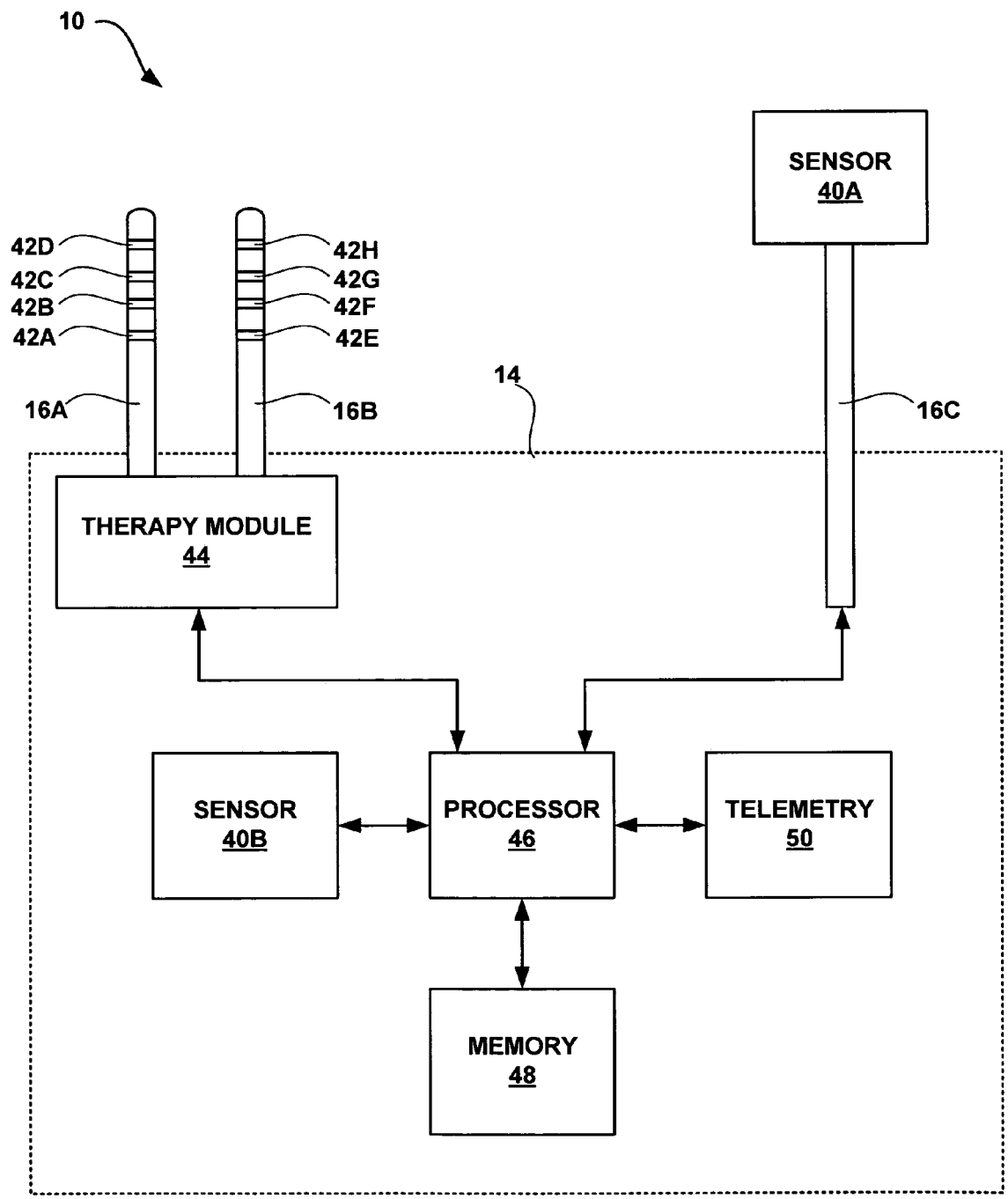
FIG. 2 is a block diagram further illustrating the example system and implantable medical device of FIG. 1.

FIG. 2 is a block diagram further illustrating system 10. In particular, FIG. 2 illustrates an example configuration of IMD 14 and leads 16A and 16B. FIG. 2 also illustrates sensors 40A and 40B (collectively "sensors 40") that output signals as a function of one or more physiological parameters of patient 12.

IMD 14 may deliver neurostimulation therapy via electrodes 42A-D of lead 16A and electrodes 42E-H of lead 16B (collectively "electrodes 42"). Electrodes 42 may be ring electrodes. The configuration, type and number of electrodes 42 illustrated in FIG. 2 are exemplary. For example, leads 16A and 16B may each include eight electrodes 42, and the electrodes 42 need not be arranged linearly on each of leads 16A and 16B.

Electrodes 42 are electrically coupled to a therapy delivery module 44 via leads 16A and 16B. Therapy delivery module 44 may, for example, include an output pulse generator coupled to a power source such as a battery. Therapy delivery module 44 may deliver electrical pulses to patient 12 via at least some of electrodes 42 under the control of a processor 46, which controls therapy delivery module 44 to deliver neurostimulation therapy according to one or more neurostimulation therapy programs selected from available programs stored in a memory 48. However, the invention is not limited to implantable neurostimulator embodiments or even to IMDs that deliver electrical stimulation. For example, in some embodiments, a therapy delivery module of an IMD may include a pump, circuitry to control the pump, and a reservoir to store a therapeutic agent for delivery via the pump, and a processor of the IMD may control delivery of a therapeutic agent by the pump according to an infusion program selected from among a plurality of infusion programs stored in a memory.

IMD 14 may also include a telemetry circuit 50 that enables processor 46 to communicate with programmers 20, 26. Via telemetry circuit 50, processor 46 may receive therapy programs specified by a clinician from clinician programmer 20 for storage in memory 48. Processor 46 may also receive program selections and therapy adjustments made by patient 12 using patient programmer 26 via telemetry circuit 50. In some embodiments, processor 46 may provide diagnostic information recorded by processor 46 and stored in memory 48 to one of programmers 20, 26 via telemetry circuit 50.

Processor 46 may include a microprocessor, a controller, a digital signal processor (DSP), an application specific integrated circuit (ASIC), a field-programmable gate array (FPGA), discrete logic circuitry, or the like. Memory 48 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. In some embodiments, memory 48 stores program instructions that, when executed by processor 46, cause IMD 14 and processor 46 to perform the functions attributed to them herein.

Each of sensors 40 outputs a signal as a function of one or more physiological parameters of patient 12. IMD 14 may include circuitry (not shown) that conditions the signals output by sensors 40 such that they may be analyzed by processor 46. For example, IMD 14 may include one or more analog to digital converters to convert analog signals output by sensors 40 into digital signals usable by processor 46, as well as suitable filter and amplifier circuitry. Although shown as including two sensors 40, system 10 may include any number of sensors.

Further, as illustrated in FIG. 2, sensors 40 may be included as part of IMD 14, or coupled to IMD 14 via leads 16. Sensors 40 may be coupled to IMD 14 via therapy leads 16A and 16B, or via other leads 16, such as lead 16C depicted in FIG. 2. In some embodiments, a sensor located outside of IMD 14 may be in wireless communication with processor 46.

As discussed above, exemplary physiological parameters of patient 12 that may be monitored by IMD 14 to determine values of one or more sleep quality metrics include activity level, posture, heart rate, ECG morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, and eye motion. Further, as discussed above, external medical device embodiments of the invention may additionally or alternatively monitor galvanic skin response. Sensors 40 may be of any type known in the art capable of outputting a signal as a function of one or more of these parameters.

In some embodiments, in order to determine one or more sleep quality metric values, processor 46 determines when patient 12 is attempting to fall asleep. For example, processor 46 may identify the time that patient begins attempting to fall asleep based on an indication received from patient 12, e.g., via clinician programmer 20 and a telemetry circuit 50. In other embodiments, processor 46 identifies the time that patient 12 begins attempting to fall asleep based on the activity level of patient 12.

In such embodiments, IMD 14 may include one or more sensors 40 that generate a signal as a function of patient activity. For example, sensors 40 may include one or more accelerometers, gyros, mercury switches, or bonded piezoelectric crystals that generates a signal as a function of patient activity, e.g., body motion, footfalls or other impact events, and the like. Additionally or alternatively, sensors 40 may include one or more electrodes that generate an electromyogram (EMG) signal as a function of muscle electrical activity, which may indicate the activity level of a patient. The electrodes may be, for example, located in the legs, abdomen, chest, back or buttocks of patient 12 to detect muscle activity associated with walking, running, or the like. The electrodes may be coupled to IMD 14 by leads 16 or wirelessly, or, if IMD 14 is implanted in these locations, integrated with a housing of IMD 14.

However, bonded piezoelectric crystals located in these areas generate signals as a function of muscle contraction in addition to body motion, footfalls or other impact events. Consequently, use of bonded piezoelectric crystals to detect activity of patient 12 may be preferred in some embodiments in which it is desired to detect muscle activity in addition to body motion, footfalls, or other impact events. Bonded piezoelectric crystals may be coupled to IMD 14 via leads 16 or wirelessly, or piezoelectric crystals may be bonded to the can of IMD 14 when the IMD is implanted in these areas, e.g., in the back, chest, buttocks or abdomen of patient 12.

Processor 46 may identify a time when the activity level of patient 12 falls below a threshold activity level value stored in memory 48, and may determine whether the activity level remains substantially below the threshold activity level value for a threshold amount of time stored in memory 48. In other words, patient 12 remaining inactive for a sufficient period of time may indicate that patient 12 is attempting to fall asleep. If processor 46 determines that the threshold amount of time is exceeded, processor 46 may identify the time at which the activity level fell below the threshold activity level value as the time that patient 12 began attempting to fall asleep.

In some embodiments, processor 46 determines whether patient 12 is attempting to fall asleep based on whether patient 12 is or is not recumbent, e.g., lying down. In such embodiments, sensors 40 may include a plurality of accelerometers, gyros, or magnetometers oriented orthogonally that generate signals which indicate the posture of patient 12. In addition to being oriented orthogonally with respect to each other, each of sensors 40 used to detect the posture of patient 12 may be generally aligned with an axis of the body of patient 12. In exemplary embodiments, IMD 14 includes three orthogonally oriented posture sensors 40.

When sensors 40 include accelerometers, for example, that are aligned in this manner, processor 46 may monitor the magnitude and polarity of DC components of the signals generated by the accelerometers to determine the orientation of patient 12 relative to the Earth's gravity, e.g., the posture of patient 12. In particular, the processor 46 may compare the DC components of the signals to respective threshold values stored in memory 48 to determine whether patient 12 is or is not recumbent. Further information regarding use of orthogonally aligned accelerometers to determine patient posture may be found in a commonly assigned U.S. Pat. No. 5,593,431, which issued to Todd J. Sheldon.

Other sensors 40 that may generate a signal that indicates the posture of patient 12 include electrodes that generate an electromyogram (EMG) signal, or bonded piezoelectric crystals that generate a signal as a function of contraction of muscles. Such sensors 40 may be implanted in the legs, buttocks, abdomen, or back of patient 12, as described above. The signals generated by such sensors when implanted in these locations may vary based on the posture of patient 12, e.g., may vary based on whether the patient is standing, sitting, or laying down.

Further, the posture of patient 12 may affect the thoracic impedance of the patient. Consequently, sensors 40 may include an electrode pair, such as one electrode integrated with the housing of IMD 14 and one of electrodes 42, that generates a signal as a function of the thoracic impedance of patient 12, and processor 46 may detect the posture or posture changes of patient 12 based on the signal. The electrodes of the pair may be located on opposite sides of the patient's thorax. For example, the electrode pair may include one of electrodes 42 located proximate to the spine of a patient for delivery of SCS therapy, and IMD 14 with an electrode integrated in its housing may be implanted in the abdomen of patient 12.

Additionally, changes of the posture of patient 12 may cause pressure changes with the cerebrospinal fluid (CSF) of the patient. Consequently, sensors 40 may include pressure sensors coupled to one or more intrathecal or intracerebroventricular catheters, or pressure sensors coupled to IMD 14 wirelessly or via lead 16. CSF pressure changes associated with posture changes may be particularly evident within the brain of the patient, e.g., may be particularly apparent in an intracranial pressure (ICP) waveform.

In some embodiments, processor 46 considers both the posture and the activity level of patient 12 when determining whether patient 12 is attempting to fall asleep. For example, processor 46 may determine whether patient 12 is attempting to fall asleep based on a sufficiently long period of subthreshold activity, as described above, and may identify the time that patient began attempting to fall asleep as the time when patient 12 became recumbent. Any of a variety of combinations or variations of these techniques may be used to determine when patient 12 is attempting to fall asleep, and a specific one or more techniques may be selected based on the sleeping and activity habits of a particular patient.

Processor 46 may also determine when patient 12 is asleep, e.g., identify the times that patient 12 falls asleep and wakes up, in order to determine one or more sleep quality metric values. The detected values of physiological parameters of patient 12, such as activity level, heart rate, values of ECG morphological features, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, eye motion, and galvanic skin response may discernibly change when patient 12 falls asleep or wakes up. In particular, these physiological parameters may be at low values when patient 12 is asleep. Further, the variability of at least some of these parameters, such as heart rate and respiration rate, may be at a low value when the patient is asleep.

Consequently, in order to detect when patient 12 falls asleep and wakes up, processor 46 may monitor one or more of these physiological parameters, or the variability of these physiological parameters, and detect the discernable changes in their values associated with a transition between a sleeping state and an awake state.

In some embodiments, in order to determine whether patient 12 is asleep, processor 46 monitors a plurality of physiological parameters, and determines a value of a metric that indicates the probability that patient 12 is asleep for each of the parameters based on a value of the parameter. In particular, the processor 46 may apply a function or look-up table to the current value, and/or the variability of each of a plurality of physiological parameters to determine a sleep probability metric value for each of the plurality of physiological parameters. A sleep probability metric value may be a numeric value, and in some embodiments may be a probability value, e.g., a number within the range from 0 to 1, or a percentage level.

Processor 46 may average or otherwise combine the plurality of sleep probability metric values to provide an overall sleep probability metric value. In some embodiments, processor 46 may apply a weighting factor to one or more of the sleep probability metric values prior to combination. Processor 46 may compare the overall sleep probability metric value to one or more threshold values stored in memory 48 to determine when patient 12 falls asleep or awakes. Use of sleep probability metric values to determine when a patient is asleep based on a plurality of monitored physiological parameters is described in greater detail in a commonly assigned and copending U.S. pat. application Ser. No. 11/081,786, by Ken Heruth and Keith Miesel, entitled "DETECTING SLEEP," bearing and filed on Mar. 16, 2005, which is incorporated herein by reference in its entirety.

To enable processor 46 to determine when patient 12 is asleep or awake, sensors 40 may include, for example, activity sensors as described above. In some embodiments, the activity sensors may include electrodes or bonded piezoelectric crystals, which may be implanted in the back, buttocks, chest, or abdomen of patient 12 as described above. In such embodiments, processor 46 may detect the electrical activation and contractions of muscles associated with gross motor activity of the patient, e.g., walking, running or the like via the signals generated by such sensors. Processor 46 may also detect spasmodic or pain related muscle activation via the signals generated by such sensors. Spasmodic or pain related muscle activation may indicate that patient 12 is not sleeping, e.g., unable to sleep, or if patient 12 is sleeping, may indicate a lower level of sleep quality.

As another example, sensors 40 may include electrodes located on leads or integrated as part of the housing of IMD 14 that output an electrogram signal as a function of electrical activity of the heart of patient 12, and processor 46 may monitor the heart rate of patient 12 based on the electrogram signal. In other embodiments, a sensor may include an acoustic sensor within IMD 14, a pressure sensor within the bloodstream or cerebrospinal fluid of patient 12, or a temperature sensor located within the bloodstream of patient 12. The signals output by such sensors may vary as a function of contraction of the heart of patient 12, and can be used by IMD 14 14 to monitor the heart rate of patient 12.

In some embodiments, processor 46 may detect, and measure values for one or more ECG morphological features within an electrogram generated by electrodes as described above. ECG morphological features may vary in a manner that indicates whether patient 12 is asleep or awake. For example, the amplitude of the ST segment of the ECG may decrease when patient 12 is asleep. Further, the amplitude of QRS complex or T-wave may decrease, and the widths of the QRS complex and T-wave may increase when patient 12 is asleep. The QT interval and the latency of an evoked response may increase when patient 12 is asleep, and the amplitude of the evoked response may decrease when patient 12 is asleep.

In some embodiments, sensors 40 may include an electrode pair, including one electrode integrated with the housing of IMD 14 and one of electrodes 16, that output a signal as a function of the thoracic impedance of patient 12 as described above, which varies as a function of respiration by patient 12. In other embodiments, sensors 40 may include a strain gauge, bonded piezoelectric element, or pressure sensor within the blood or CSF that outputs a signal that varies based on patient respiration. An electrogram output by electrodes as discussed above may also be modulated by patient respiration, and may be used as an indirect representation of respiration rate.

Sensors 40 may include electrodes that output an electromyogram (EMG) signal as a function of muscle electrical activity, as described above, or may include any of a variety of known temperature sensors to output a signal as a function of a core or subcutaneous temperature of patient 12. Such electrodes and temperature sensors may be incorporated within the housing of IMD 14, or coupled to IMD 14 wirelessly or via leads. Sensors 40 may also include a pressure sensor within, or in contact with, a blood vessel. The pressure sensor may output a signal as a function of the blood pressure of patient 12, and may, for example, comprise a Chronicle Hemodynamic Monitor™ commercially available from Medtronic, Inc. of Minneapolis, Minn. Further, certain muscles of patient 12, such as the muscles of the patient's neck, may discernibly relax when patient 12 is asleep or within certain sleep states. Consequently, sensors 40 may include strain gauges or EMG electrodes implanted in such locations that generate a signal as a function of muscle tone.

Sensors 40 may also include optical pulse oximetry sensors or Clark dissolved oxygen sensors located within, as part of a housing of, or outside of IMD 14, which output signals as a function blood oxygen saturation and blood oxygen partial pressure respectively. In some embodiments, system 10 may include a catheter with a distal portion located within the cerebrospinal fluid of patient 12, and the distal end may include a Clark dissolved oxygen sensor to output a signal as a function of the partial pressure of oxygen within the cerebrospinal fluid. Embodiments in which an IMD comprises an implantable pump, for example, may include a catheter with a distal portion located in the cerebrospinal fluid.

In some embodiments, sensors 40 may include one or more intraluminal, extraluminal, or external flow sensors positioned to output a signal as a function of arterial blood flow. A flow sensor may be, for example, an electromagnetic, thermal convection, ultrasonic-Doppler, or laser-Doppler flow sensor. Further, in some external medical device embodiments of the invention, sensors 40 may include one or more electrodes positioned on the skin of patient 12 to output a signal as a function of galvanic skin response.

Additionally, in some embodiments, sensors 40 may include one or more electrodes positioned within or proximate to the brain of patient, which detect electrical activity of the brain. For example, in embodiments in which IMD 14 delivers stimulation or other therapy to the brain, processor 46 may be coupled to electrodes implanted on or within the brain via a lead 16. In other embodiments, processor 46 may be wirelessly coupled to electrodes that detect brain electrical activity.

For example, one or more modules may be implanted beneath the scalp of the patient, each module including a housing, one or more electrodes, and circuitry to wirelessly transmit the signals detected by the one or more electrodes to IMD 14. In other embodiments, the electrodes may be applied to the patient's scalp, and electrically coupled to a module that includes circuitry for wirelessly transmitting the signals detected by the electrodes to IMD 14. The electrodes may be glued to the scalp, or a headband, hair net, cap, or the like may incorporate the electrodes and the module, and may be worn by patient 12 to apply the electrodes to the patient's scalp when, for example, the patient is attempting to sleep. The signals detected by the electrodes and transmitted to IMD 14 may be electroencephalogram (EEG) signals, and processor 46 may process the EEG signals to detect when patient 12 is asleep using any of a variety of known techniques, such as techniques that identify whether a patient is asleep based on the amplitude and/or frequency of the EEG signals.

Also, the motion of the eyes of patient 12 may vary depending on whether the patient is sleeping and which sleep state the patient is in. Consequently, sensors 40 may include electrodes place proximate to the eyes of patient 12 to detect electrical activity associated with motion of the eyes, e.g., to generate an electro-oculography (EOG) signal. Such electrodes may be coupled to IMD 14 via one or more leads 16, or may be included within modules that include circuitry to wirelessly transmit detected signals to IMD 14. Wirelessly coupled modules incorporating electrodes to detect eye motion may be worn externally by patient 12, e.g., attached to the skin of patient 12 proximate to the eyes by an adhesive when the patient is attempting to sleep.

Processor 46 may also detect arousals and/or apneas that occur when patient 12 is asleep based on one or more of the above-identified physiological parameters. For example, processor 46 may detect an arousal based on an increase or sudden increase in one or more of heart rate, heart rate variability, respiration rate, respiration rate variability, blood pressure, or muscular activity as the occurrence of an arousal. Processor 46 may detect an apnea based on a disturbance in the respiration rate of patient 12, e.g., a period with no respiration.

Processor 46 may also detect arousals or apneas based on sudden changes in one or more of the ECG morphological features identified above. For example, a sudden elevation of the ST segment within the ECG may indicate an arousal or an apnea. Further, sudden changes in the amplitude or frequency of an EEG signal, EOG signal, or muscle tone signal may indicate an apnea or arousal. Memory 48 may store thresholds used by processor 46 to detect arousals and apneas. Processor 46 may determine, as a sleep quality metric value, the number of apnea events and/or arousals during a night.

Further, in some embodiments, processor 46 may determine which sleep state patient 12 is in during sleep, e.g., REM, S1, S2, S3, or S4, based on one or more of the monitored physiological parameters. In some embodiments, memory 48 may store one or more thresholds for each of sleep states, and processor 46 may compare physiological parameter or sleep probability metric values to the thresholds to determine which sleep state patient 12 is currently in. Processor 46 may determine, as sleep quality metric values, the amounts of time per night spent in the various sleep states. Further, in some embodiments, processor 46 may use any of a variety of known techniques for determining which sleep state patient is in based on an EEG signal, which processor 46 may receive via electrodes as described above, such as techniques that identify sleep state based on the amplitude and/or frequency of the EEG signals. In some embodiments, processor 46 may also determine which sleep state patient is in based on an EOG signal, which processor 46 may receive via electrodes as described above, either alone or in combination with an EEG signal, using any of a variety of techniques known in the art. Inadequate time spent in deeper sleep states, e.g., S3 and S4, is an indicator of poor sleep quality.

Figure 3:
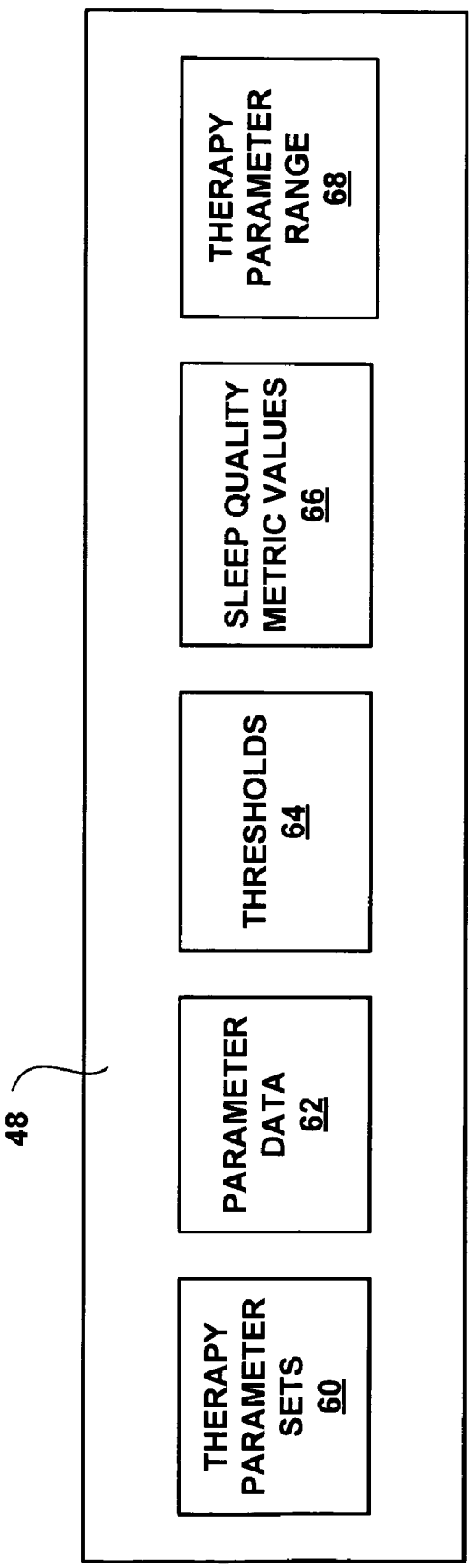
FIG. 3 is a block diagram illustrating an example memory of the implantable medical device of FIG. 1.

FIG. 3 further illustrates memory 48 of IMD 14. As illustrated in FIG. 3, memory 48 stores a plurality of therapy parameter sets 60. Therapy parameter sets 60 may include parameter sets randomly or non-randomly generated by processor 46 over therapy parameter ranges 68 set by a clinician using clinician programmer 20. Therapy parameter sets 60 may also include parameter sets specified by a clinician using clinician programmer 20 and preprogrammed therapy parameter sets.

Memory 48 may also include parameter data 62 recorded by processor 46, e.g., physiological parameter values, or mean or median physiological parameter values. Memory 48 stores threshold values 64 used by processor 46 in the collection of sleep quality metric values, as discussed above. In some embodiments, memory 48 also stores one or more functions or look-up tables (not shown) used by processor 46 to determine sleep probability metric values, or to determine an overall sleep quality metric value.

Further, processor 46 stores determined sleep quality metric values 66 for each of the plurality of therapy parameter sets 60 within memory 48. Processor 46 conducts a sensitivity analysis of the sleep quality metric values for each therapy parameter. The sensitivity analysis determines a value for each therapy parameter that defines a substantially maximum sleep quality metric value. In other words, the sensitivity analysis identifies parameter values that yield the best sleep quality metric values. Processor 46 then determines a baseline therapy parameter set based on the sensitivity analysis and stores the baseline therapy parameter set with therapy parameter set 66 or separately within memory 48. The baseline therapy parameter set may be identical to a single one of therapy parameter sets 60, or may be a new therapy parameter set that includes one or more therapy parameter values from a plurality of therapy parameter sets 60. The baseline therapy parameter set includes the values for respective therapy parameters that produced the best sleep quality metric values.

Processor 46 may collect sleep quality metric values 66 each time patient 12 sleeps, or only during selected times that patient 12 is asleep. Processor 46 may store each sleep quality metric value determined within memory 48 as a sleep quality metric value 66. Further, processor 46 may apply a function or look-up table to a plurality of sleep quality metric values to determine overall sleep quality metric value, and may store the overall sleep quality metric values within memory 48. The application of a function or look-up table by processor 46 for this purpose may involve the use of weighting factors for one or more of the individual sleep quality metric values.

In some embodiments, as discussed above, processor 46 may adjust the therapy delivered by therapy module 44 based on a change in the sleep quality metric value. In particular, processor 46 may perturb one or more therapy parameters of the baseline therapy parameter set, such as pulse amplitude, pulse width, pulse rate, duty cycle, and duration to determine if the current sleep quality metric value improves or worsens during perturbation. In some embodiments, processor 46 may iteratively and incrementally increase or decrease values of the therapy parameters until a substantially maximum value of the sleep quality metric value is again determined.

Figure 4:
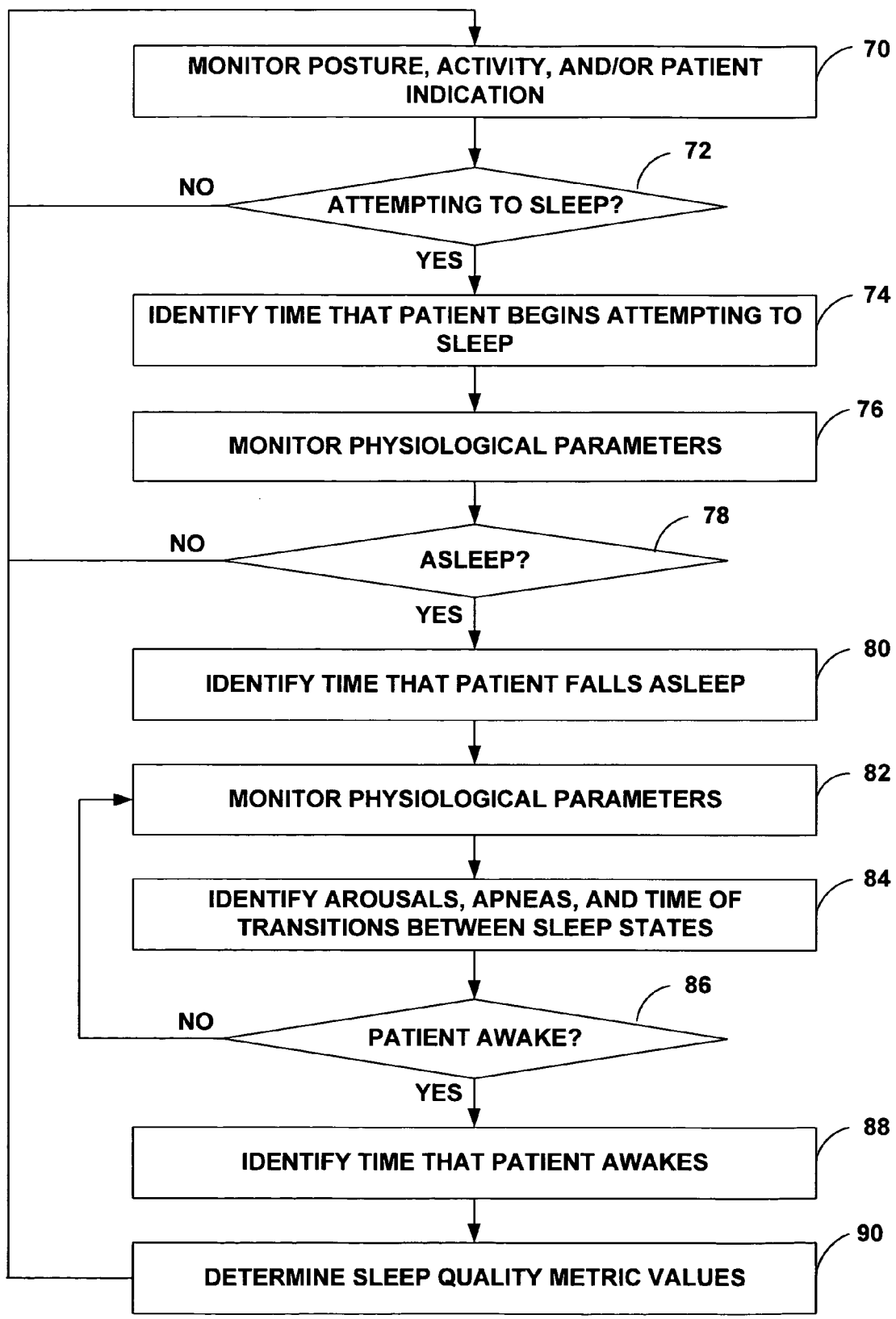
FIG. 4 is a flow diagram illustrating an example method for collecting sleep quality information that may be employed by an implantable medical device.

FIG. 4 is a flow diagram illustrating an example method for collecting sleep quality information that may be employed by IMD 14 alone, or in combination with a computing device and/or a monitor. In some embodiments, as discussed above, a computing device, such as one of programmers 20 and 26, may determine sleep quality metric values based on monitored physiological parameter values, rather than IMD 14. Further, in some embodiments, a monitor may monitor physiological parameter values instead of, or in addition to, IMD 14.

In the illustrated example, however, IMD 14 monitors the posture and/or activity level of patient 12, or monitors for an indication from patient 12, e.g., via patient programmer 26 (70), and determines whether patient 12 is attempting to fall asleep based on the posture, activity level, and/or a patient indication, as described above (72). If IMD 14 determines that patient 12 is attempting to fall asleep, IMD 14 identifies the time that patient 12 began attempting to fall asleep using any of the techniques described above (74), and monitors one or more of the various physiological parameters of patient 12 discussed above to determine whether patient 12 is asleep (76, 78).

In some embodiments, IMD 14 compares parameter values or parameter variability values to one or more threshold values 64 to determine whether patient 12 is asleep. In other embodiments, IMD 14 applies one or more functions or look-up tables to determine one or more sleep probability metric values based on the physiological parameter values, and compares the sleep probability metric values to one or more threshold values 64 to determine whether patient 12 is asleep. While monitoring physiological parameters (76) to determine whether patient 12 is asleep (78), IMD 14 may continue to monitor the posture and/or activity level of patient 12 (70) to confirm that patient 12 is still attempting to fall asleep (72).

When IMD 14 determines that patient 12 is asleep, e.g., by analysis of the various parameters contemplated herein, IMD 14 will identify the time that patient 12 fell asleep (80). While patient 12 is sleeping, IMD 14 will continue to monitor physiological parameters of patient 12 (82). As discussed above, IMD 14 may identify the occurrence of arousals and/or apneas based on the monitored physiological parameters (84). Further, IMD 14 may identify the time that transitions between sleep states, e.g., REM, S1, S2, S3, and S4, occur based on the monitored physiological parameters (84).

Additionally, while patient 12 is sleeping, IMD 14 monitors physiological parameters of patient 12 (82) to determine whether patient 12 has woken up (86). When IMD 14 determines that patient 12 is awake, IMD 14 identifies the time that patient 12 awoke (88), and determines sleep quality metric values based on the information collected while patient 12 was asleep (90).

For example, one sleep quality metric value that IMD 14 may calculate is sleep efficiency, which IMD 14 may calculate as a percentage of time during which patient 12 is attempting to sleep that patient 12 is actually asleep. IMD 14 may determine a first amount of time between the time IMD 14 identified that patient 12 fell asleep and the time IMD 14 identified that patient 12 awoke. IMD may also determine a second amount of time between the time IMD 14 identified that patient 12 began attempting to fall asleep and the time IMD 14 identified that patient 12 awoke. To calculate the sleep efficiency, IMD 14 may divide the first time by the second time.

Another sleep quality metric value that IMD 14 may calculate is sleep latency, which IMD 14 may calculate as the amount of time between the time IMD 14 identified that patient 12 was attempting to fall asleep and the time IMD 14 identified that patient 12 fell asleep. Other sleep quality metrics with values determined by IMD 14 based on the information collected by IMD 14 in the illustrated example include: total time sleeping per day, at night, and during daytime hours; number of apnea and arousal events per occurrence of sleep; and amount of time spent in the various sleep states. IMD 14 may store the determined values as sleep quality metric values 66 within memory 48.

IMD 14 may perform the example method illustrated in FIG. 4 continuously. For example, IMD 14 may monitor to identify when patient 12 is attempting to sleep and asleep any time of day, each day. In other embodiments, IMD 14 may only perform the method during evening hours and/or once every N days to conserve battery and memory resources. Further, in some embodiments, IMD 14 may only perform the method in response to receiving a command from patient 12 or a clinician via one of programmers 20, 26. For example, patient 12 may direct IMD 14 to collect sleep quality information at times when the patient believes that his or her sleep quality is low or therapy is ineffective.

Figure 5:
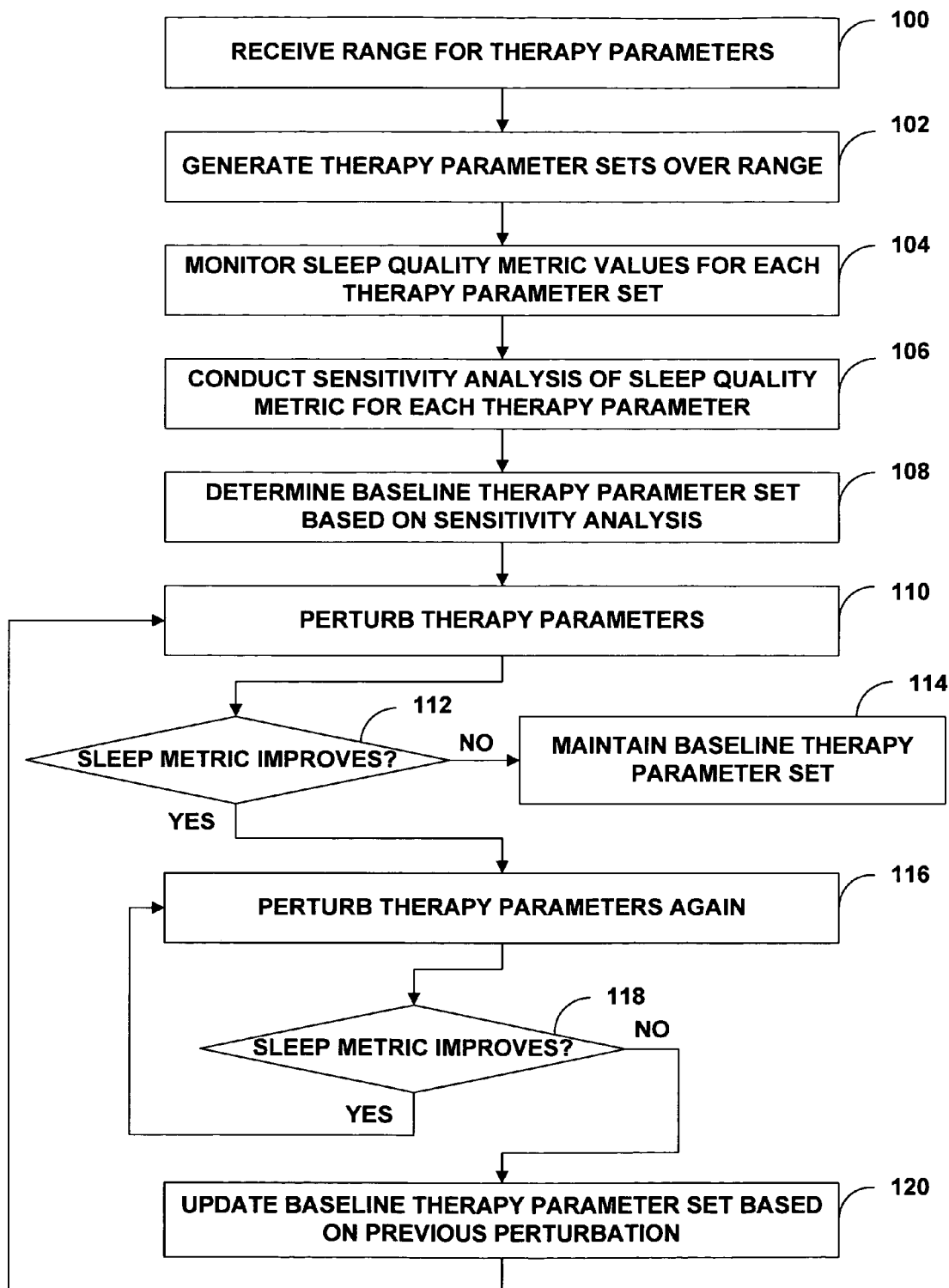
FIG. 5 is a flow diagram illustrating an example method for identifying and modifying a baseline therapy parameter set based on a sensitivity analysis of a sleep quality metric, which is an example of a performance metric.

FIG. 5 is a flow diagram illustrating an example method for identifying and modifying a baseline therapy parameter set based on a sensitivity analysis of a sleep quality metric, which is an example of a performance metric. In the illustrated example, the method is employed by IMD 14. However, in other embodiments, a system including one or more of IMD 14, a physiological parameter monitor, a trial therapy device, and a programmer and/or other computing device may perform the example method, as described above.

IMD 14 receives a therapy parameter range 68 for therapy parameters (100) from a clinician using clinician programmer 20 via telemetry circuit 50. The range 68 may include minimum and maximum values for each of one or more individual therapy parameters, such as pulse amplitude, pulse width, pulse rate, duty cycle, duration, dosage, infusion rate, electrode placement, and electrode selection. Range 68 may be stored in memory 48, as described in reference to FIG. 3. Processor 46 then randomly or non-randomly generates a plurality of therapy parameter sets 60 with individual parameter values selected from the range 68 (102). The generated therapy parameter sets 60 may substantially cover range 68, but do not necessarily include each and every therapy parameter value within range 68, or every possible combination of therapy parameters within range 68. Therapy parameter sets 60 may also be stored in memory 48.

IMD 14 monitors a sleep quality metric of patient 12 for each of the randomly or non-randomly generated therapy parameter sets 60 spanning range 68 (104). The values of the sleep quality metric 66 corresponding to each of the therapy parameter sets 60 may be stored in memory 48 of IMD 14. IMD 14 then conducts a sensitivity analysis of the sleep quality metric for each of the therapy parameters (106). The sensitivity analysis determines a value for each of the therapy parameters that produced a substantially maximum value of the sleep quality metric. A baseline therapy parameter set is then determined based on the therapy parameter values from the sensitivity analysis (108). The baseline therapy parameter set includes a combination of the therapy parameter values individually observed to produce a substantially maximum sleep quality metric. In some embodiments, the patient may enter comments, a pain value from a scale, or other feedback used along with the sensitivity analysis to determine the baseline parameter set. The baseline therapy parameter set may also be stored with therapy parameters sets 60 in memory 48. In some embodiments, the baseline therapy parameter set may be stored separately from the generated therapy parameter sets.

IMD 14 controls delivery of the therapy based on the baseline therapy parameter set. Periodically during the therapy, IMD 14 checks to ensure that the baseline therapy parameter continues to define a substantially maximum sleep quality metric value for patient 12. IMD 14 first perturbs at least one of the therapy parameter values of the baseline therapy parameter set (110). The perturbation comprises incrementally increasing and/or decreasing the therapy parameter value. A perturbation period may be preset to occur at a specific time, in response to a physiological parameter monitored by the IMD, or in response to a signal from the patient or clinician. The perturbation may be applied for a single selected parameter or two or more parameters, or all parameters in the baseline therapy parameter set. Hence, numerous parameters may be perturbed in sequence. For example, upon perturbing a first parameter and identifying a value that produces a maximum metric value, a second parameter may be perturbed with the first parameter value fixed at the identified value. This process may continue for each of the parameters in the therapy parameter set.

Upon perturbing a parameter value, IMD 14 then compares a value of the sleep quality metric defined by the perturbed therapy parameter set to the value of the sleep quality metric defined by the baseline therapy parameter set (112). If the sleep quality metric value does not improve with the perturbation, IMD 14 maintains the unperturbed baseline therapy parameter set values (114). If the sleep quality metric value does improve with the perturbation, IMD 14 perturbs the therapy parameter value again (116) in the same direction that defined the previous improvement in the sleep quality metric value. IMD 14 compares a value of the sleep quality metric defined by the currently perturbed therapy parameter set and the sleep quality metric value defined by the previously perturbed therapy parameter set (118). If the sleep metric value does not improve, IMD 14 updates the baseline therapy parameter set based on the therapy parameter values from the previous perturbation (120). If the sleep metric value improves again, IMD 14 continues to perturb the therapy parameter value (116).

Periodically checking the value of the sleep quality metric for the baseline therapy parameter set allows IMD 14 to consistently deliver a therapy to patient 12 that defines a substantially maximum sleep quality metric value of patient 12. This allows the patient's symptoms to be continually managed even as the patient's physiological parameters change.

In some embodiments, an external computing device, such as clinician programmer 20, may generate the plurality of therapy parameter sets over the range. A clinician may then provide the therapy parameter sets to IMD 14 via clinician programmer 20. The computing device may provide individual therapy parameter sets to be tested, and may thus control the testing by IMD 14, or may provide a listing of therapy parameter sets to be tested.

Furthermore, an external computing device, such as programmer 20, a separate desktop computer, or server, may receive the sleep quality metric values collected by the IMD for the plurality of therapy parameter sets. The external computing device may then conduct the sensitivity analysis to determine the baseline therapy parameter set. The external computing device may also control the subsequent perturbations. In some embodiments, the external computing device may receive physiological parameter values from IMD 14, and, rather that IMD 14, the external computing device may determine values of the sleep quality or other performance metric based on the physiological parameter values received from IMD 14.

In some embodiments, the sensitivity analysis and determination of a baseline therapy parameter set may be performed as part of a trialing process. In such embodiments, an external or implanted trial therapy device, such as a trial neurostimulator, may perform the functions ascribed to IMD 14 above that are associated with performing the sensitivity analysis and determination of a baseline therapy parameter set. The trial therapy device may include a therapy module 44, processor 46, and memory 48, and may be coupled to sensors 40 and leads 16, as described above with reference to IMD 14 and FIGS. 2 and 3.

IMD 14 may then be implanted in patient 12, and programmed to deliver therapy according to the baseline therapy parameter set. In such embodiments, IMD 14 may perform the perturbation and updating functions of the example method illustrated by FIG. 5. In some embodiments, an external computing device may control delivery of a plurality of therapy parameter sets by the trial device, determine performance metric values based on physiological parameter values received from the trial device, and/or perform the sensitivity analysis.

Figure 6:
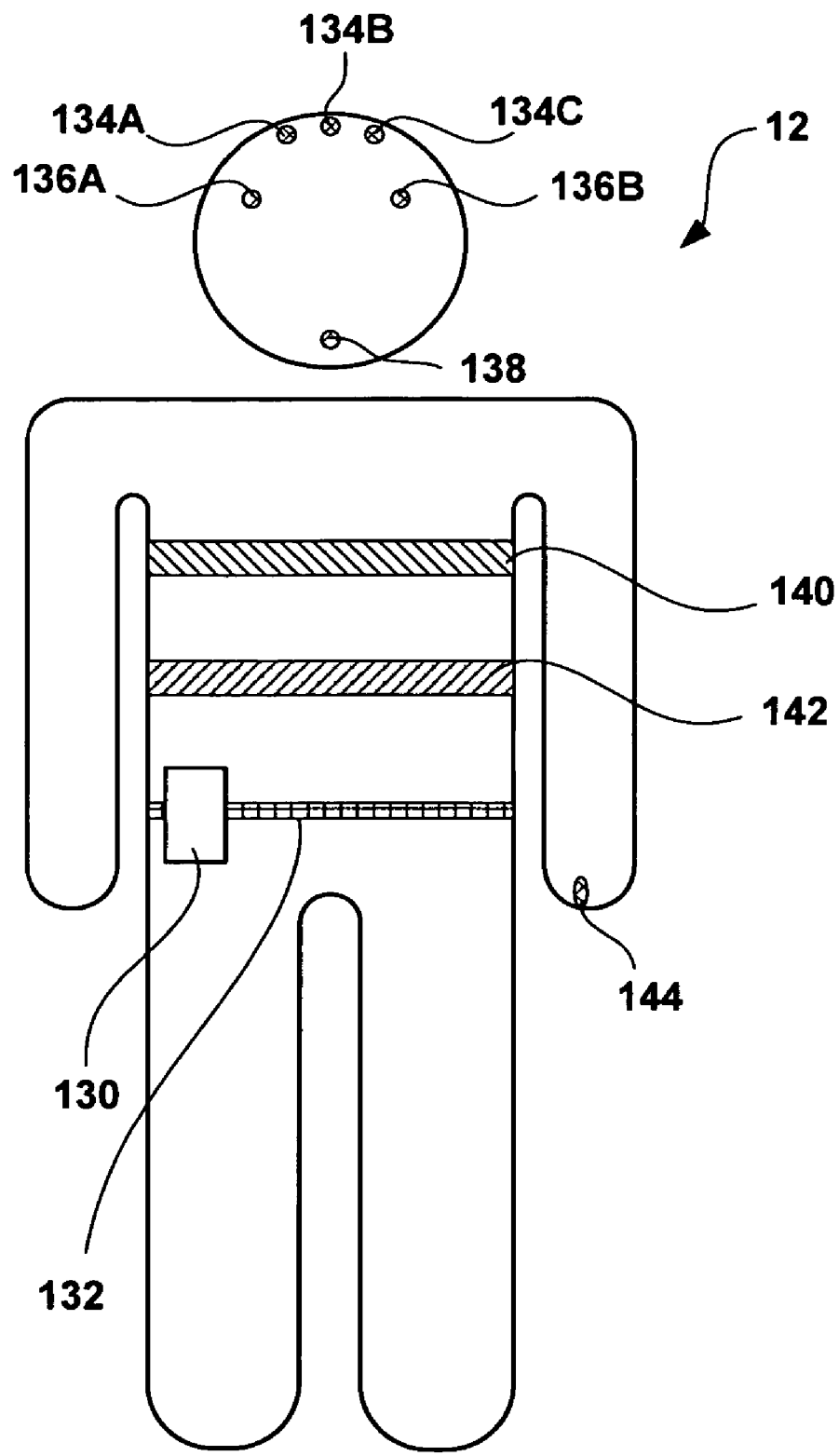
FIG. 6 is a conceptual diagram illustrating a monitor that monitors values of one or more physiological parameters of a patient.

FIG. 6 illustrates, a separate monitor 130 that monitors values of one or more physiological parameters of patient 12 instead of, or in addition to the trial device or IMD 14. Monitor 130 may include a processor 46 and memory 48, and may be coupled to sensors 40, as illustrated above with reference to IMD 14 and FIGS. 2 and 3. Monitor 130 may identify performance metric values based on the values of the monitored physiological parameter values, or may transmit the physiological parameter values to a computing device for determination of the performance metric values. In some embodiments, an external computing device, such as a programming device, may incorporate monitor 130. In the illustrated embodiment, monitor 130 is portable, and is configured to be attached to or otherwise carried by a belt 132, and may thereby be worn by patient 12.

FIG. 6 also illustrates various sensors 40 that may be coupled to monitor 130 by leads, wires, cables, or wireless connections, such as EEG electrodes 134A-C placed on the scalp of patient 12, a plurality of EOG electrodes 136A and 136B placed proximate to the eyes of patient 12, and one or more EMG electrodes 138 placed on the chin or jaw the patient. The number and positions of electrodes 134, 136 and 138 illustrated in FIG. 6 are exemplary. For example, although only three EEG electrodes 13 are illustrated in FIG. 1, an array of between 16 and 25 EEG electrodes 143 may be placed on the scalp of patient 12, as is known in the art. EEG electrodes 134 may be individually placed on patient 12, or integrated within a cap or hair net worn by the patient.

In the illustrated example, patient 12 wears an ECG belt 140. ECG belt 140 incorporates a plurality of electrodes for sensing the electrical activity of the heart of patient 12. The heart rate and, in some embodiments, ECG morphology of patient 12 may monitored by monitor 130 based on the signal provided by ECG belt 140. Examples of suitable belts 140 for sensing the heart rate of patient 12 are the "M" and "F" heart rate monitor models commercially available from Polar Electro. In some embodiments, instead of belt 140, patient 12 may wear a plurality of ECG electrodes attached, e.g., via adhesive patches, at various locations on the chest of the patient, as is known in the art. An ECG signal derived from the signals sensed by such an array of electrodes may enable both heart rate and ECG morphology monitoring, as is known in the art.

As shown in FIG. 6, patient 12 may also wear a respiration belt 142 that outputs a signal that varies as a function of respiration of the patient. Respiration belt 142 may be a plethysmograpy belt, and the signal output by respiration belt 142 may vary as a function of the changes in the thoracic or abdominal circumference of patient 12 that accompany breathing by the patient. An example of a suitable belt 142 is the TSD201 Respiratory Effort Transducer commercially available from Biopac Systems, Inc. Alternatively, respiration belt 142 may incorporate or be replaced by a plurality of electrodes that direct an electrical signal through the thorax of the patient, and circuitry to sense the impedance of the thorax, which varies as a function of respiration of the patient, based on the signal. In some embodiments, ECG and respiration belts 140 and 142 may be a common belt worn by patient 12, and the relative locations of belts 140 and 142 depicted in FIG. 6 are exemplary.

In the example illustrated by FIG. 1, patient 12 also wears a transducer 144 that outputs a signal as a function of the oxygen saturation of the blood of patient 12. Transducer 144 may be an infrared transducer. Transducer 144 may be located on one of the fingers or earlobes of patient 12. Sensors 40 coupled to monitor 130 may additionally or alternatively include any of the variety of sensors described above that monitor any one or more of activity level, posture, heart rate, ECG morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, eye motion, and galvanic skin response.

FIG. 6 also illustrates an external trial therapy device 146 in conjunction with patient 12. In the illustrated example, patient 12 wears trial therapy device 146 with monitor 130 on belt 132. The trial therapy device 146 may be coupled to one or more transcutaneoulsy implanted leads or catheters for delivery of therapy, such as neurostimulation or a drug, to patient 12. As described above, trial therapy device 146 may deliver therapy to patient 12 during the sensitivity analysis and baseline therapy parameter set determination portion of the method illustrated in FIG. 5 and, in some embodiments, may also monitor physiological parameters of patient 12, determine performance metric values, and/or perform the sensitivity analysis to determine the baseline therapy parameter set for use by IMD 14.

Various embodiments of the invention have been described. However one skilled in the art will appreciate, however, that various modifications may be made to the described embodiments without departing from the scope of the invention. For example, although described herein primarily in the context of treatment of pain with an implantable neurostimulator or implantable pump, the invention is not so limited. Moreover, the invention is not limited to implantable medical devices. The invention may be embodied in any implantable or external medical device that delivers therapy to treat any ailment of symptom of a patient.

As another example, the invention has been primarily described in the context of monitoring a sleep quality metric; however the invention is not so limited. The invention may monitor any performance metric, such as an activity metric, posture metric, a movement disorder metric, or other metrics that indicate the efficacy or degree of side effects associated a therapy delivered to a patient.

In some embodiments, for example, IMD 14 or any of the other devices described herein may periodically determine an activity level of patient 12 during delivery of therapy to the patient according to a plurality of parameter sets by monitoring at least one signal that is generated by a sensor 40 and varies as a function of patient activity, as described above. A value of at least one activity metric for each of a plurality of therapy parameter sets may be determined based on the activity levels associated with that parameter set. An activity metric value may be, for example, a mean or median activity level, such as an average number of activity counts per unit time. In other embodiments, an activity metric value may be chosen from a predetermined scale of activity metric values based on comparison of a mean or median activity level to one or more threshold values. The scale may be numeric, such as activity metric values from 1-10, or qualitative, such as low, medium or high activity.

In some embodiments, each activity level associated with a therapy parameter set is compared with the one or more thresholds, and percentages of time above and/or below the thresholds are determined as one or more activity metric values for that therapy parameter set. In other embodiments, each activity level associated with a therapy parameter set is compared with a threshold, and an average length of time that consecutively determined activity levels remain above the threshold is determined as an activity metric value for that therapy parameter set. One or both of the medical device or a programming device may determine the activity metric values as described herein.

As another example, the device may monitor one or more signals that are generated by respective sensors 40 and vary as a function of patient posture, as described above. Posture events are identified based on the posture of the patient, e.g., the patient's posture and/or posture transitions are periodically identified, and each identified posture event is associated with the current therapy parameter set.

A value of at least one posture metric is determined for each of the therapy parameter sets based on the posture events associated with that parameter set. A posture metric value may be, for example, an amount or percentage of time spent in a posture while a therapy parameter set is active, e.g., average amount of time over a period of time, such as an hour, that a patient was within a particular posture. In some embodiments, a posture metric value may be an average number of posture transitions over a period of time, e.g., an hour, that a particular therapy parameter sets was active.

In embodiments in which a plurality of posture metrics are determined for each therapy parameter set, an overall posture metric may be determined based on the plurality of posture metrics. The plurality of posture metrics may be used as indices to select an overall posture metric from a look-up table comprising a scale of potential overall posture metrics. The scale may be numeric, such as overall posture metric values from 1-10.

Similarly, a device may sense physiological parameter values of a patient indicative of movement disorders, such as tremor, via one or more sensors 40, such as one or more accelerometers. Movement disorder metrics values that may be determined include mean or median values output by the sensors, amounts of time the sensor signal is above or below a threshold, or frequency of episodes above or below a threshold.

Further details regarding activity and posture metric values may be found in U.S.patent application Ser. No. 11/081,785 , by, by Ken Heruth and Keith Miesel, entitled "COLLECTING ACTIVITY INFORMATION TO EVALUATE THERAPY," and filed on Mar.16, 2005, and U.S. patent application Ser. No.11/081,872, by Ken Heruth and Keith Miesel, entitled "COLLECTING POSTURE INFORMATION TO EVALUATE THERAPY," and filed on Mar.16 2005. The content of these applications is incorporated herein by reference in its entirety.

Additionally, as discussed above, feedback entered by patient 12, may be used as a performance metric instead of, or in addition to, the other performance metrics described herein. One of programming devices 20, 26 may receive the feedback from patient 12. In embodiments in which another device, such as a medical device or other computing device, performs the sensitivity analysis, the programming device may provide the feedback or performance metric values derived from the feedback to the other device. As examples, the feedback may include comments, or numeric values for pain, efficacy, or side effect levels.

For example, the programming device 20, 26 may prompt patient 12 for feedback after a new or modified program is delivered by a therapy-delivering medical device during the sensitivity analysis or perturbation portions of the method illustrated by FIG. 5. Additionally or alternatively, if patient 12 experiences discomfort, the patient could cause the sensitivity analysis or perturbation to "step backward" to the most recent setting before the setting was changed by the algorithm via the programming device. A perturbation of a therapy parameter may produce results, either related or unrelated to the performance metric, that the patient does not like. For example, a perturbation to a higher drug dosage may result in somnolence, or a perturbation to a higher SCS amplitude may painfully stimulate ribs or abdominal muscles. The patient may cause the sensitivity analysis or perturbation to "step backward" to the most recent setting to rapidly stop the undesirably results.

When the patient causes the algorithm to step backward, the device performing the sensitivity analysis or perturbation may record this as a low performance metric value for the avoided program, or may prevent further program testing, perturbation, or other program selection of the avoided program, or within in a zone of therapy parameters determined based on the avoided program. In embodiments in which feedback is used in addition to one or more other performance metrics, a clinician or physician may determine a weighting scheme to provide more or less significance to the patient's feedback, i.e., the physician may choose to give the patient feedback zero weight and instead rely completely on other performance metric values, or the physician may judge that the patient has enough perspective to be able to competently gage pain levels and input substantially objective feedback into the sensitivity analysis.

These and other embodiments are within the scope of the following claims.

The invention claimed is:

1. A method comprising:
   delivering a therapy to a patient via a medical device according to each of a plurality of therapy parameter sets, each of the parameter sets including a value for each of a plurality of therapy parameters;
   monitoring a value of a performance metric of the patient in response to therapy delivered according to each of the plurality of therapy parameter sets, wherein the performance metric comprises a sleep quality metric;
   conducting a sensitivity analysis of the performance metric for each of the plurality of therapy parameters based on the monitored values of the performance metric; and
   identifying a baseline value for each of the therapy parameters based on the sensitivity analysis to form a baseline therapy parameter set.

2. The method of claim 1, further comprising receiving a range for at least one therapy parameter in the therapy parameter sets and generating the plurality of therapy parameter sets with different values of the therapy parameter distributed over the range.

3. The method of claim 1, wherein identifying a value comprises identifying a value corresponding to one of a maximum value and a minimum value of the performance metric.

4. The method of claim 1, further comprising delivering the therapy to the patient based on a baseline therapy parameter set.

5. The method of claim 4, wherein delivering the therapy to the patient based on a baseline therapy parameter set comprises delivering the therapy to the patient via one of the medical device or another medical device.

6. The method of claim 4, further comprising perturbing at least one therapy parameter value of the baseline therapy parameter set, monitoring a perturbed value of the performance metric in response to the perturbed therapy parameter value, comparing the perturbed value of the performance metric to the value of the performance metric for the baseline therapy parameter set and adjusting the baseline therapy parameter set based on the comparison.

7. The method of claim 1, wherein the performance metric comprises a patient feedback metric.

8. A medical device comprising:
   a therapy module to deliver a therapy to a patient according to each of a plurality of therapy parameter sets, each of the therapy parameter sets including a value for each of a plurality of therapy parameters; and
   a processor to monitor a value of a performance metric of the patient in response to therapy delivered according to each of the plurality of therapy parameter sets, wherein the performance metric comprises a sleep quality metric, conduct a sensitivity analysis of the performance metric for each of the plurality of therapy parameters based on the monitored values of the performance metric, and identify a baseline value for each of the therapy parameters based on the sensitivity analysis to form a baseline therapy parameter set.

9. The medical device of claim 8, further comprising telemetry circuitry to receive a range for at least one therapy parameter in the therapy parameter sets, wherein the processor generates the plurality of therapy parameter sets with different values of the therapy parameter distributed over the range.

10. The medical device of claim 8, further comprising a memory to store a range for at least one therapy parameter in the therapy parameter sets, wherein the processor generates the plurality of therapy parameter sets with different values of the therapy parameter distributed over the range and stores the plurality of therapy parameter sets in the memory.

11. The medical device of claim 8, wherein the processor controls delivery of the therapy by the therapy module according to a baseline therapy parameter set.

12. The medical device of claim 11, wherein the processor perturbs at least one therapy parameter value of the baseline therapy parameter set, monitors a perturbed value of the performance metric in response to the perturbed therapy parameter value, compares the perturbed value of the performance metric to the value of the performance metric for the baseline therapy parameter set and adjusts the baseline therapy parameter set based on the comparison.

13. The medical device of claim 8, wherein the processor monitors a patient feedback metric.

14. The medical device of claim 8, wherein the medical device comprises an implantable medical device.

15. The medical device of claim 8, wherein the medical device comprises at least one of a neurostimulator or a pump.

16. The medical device of claim 8, wherein the medical device comprises at least one of a trial neurostimulator or a trial pump.

17. The medical device of claim 8, wherein the medical device delivers the therapy to the patient to treat chronic pain.

\* \* \* \* \*